(12) United States Patent
Shroyer et al.

(10) Patent No.: US 11,092,603 B2
(45) Date of Patent: Aug. 17, 2021

(54) KERATIN 17 AS A PROGNOSTIC MARKER FOR PANCREATIC CANCER

(71) Applicant: The Research Foundation for The State University of New York, Albany, NY (US)

(72) Inventors: Kenneth R. Shroyer, Setauket, NY (US); Luisa F. Escobar-Hoyos, Calverton, NY (US)

(73) Assignee: The Research Foundation for The State University of New York, Albany, NY (US)

(*) Notice: Subject to any disclaimer, the term of this patent is extended or adjusted under 35 U.S.C. 154(b) by 333 days.

(21) Appl. No.: 15/771,754

(22) PCT Filed: Oct. 27, 2016

(86) PCT No.: PCT/US2016/059049
§ 371 (c)(1),
(2) Date: Apr. 27, 2018

(87) PCT Pub. No.: WO2017/075174
PCT Pub. Date: May 4, 2017

(65) Prior Publication Data
US 2018/0340935 A1 Nov. 29, 2018

Related U.S. Application Data

(60) Provisional application No. 62/248,118, filed on Oct. 29, 2015.

(51) Int. Cl.
| | |
|---|---|
| *G01N 33/574* | (2006.01) |
| *C07K 16/30* | (2006.01) |
| *C07K 16/18* | (2006.01) |
| *C12Q 1/6886* | (2018.01) |
| *C12Q 1/68* | (2018.01) |
| *G01N 33/541* | (2006.01) |

(52) U.S. Cl.
CPC ....... *G01N 33/57438* (2013.01); *C07K 16/18* (2013.01); *C07K 16/30* (2013.01); *C12Q 1/68* (2013.01); *C12Q 1/6886* (2013.01); *G01N 33/541* (2013.01); *C12Q 2600/106* (2013.01); *C12Q 2600/158* (2013.01); *G01N 2333/4742* (2013.01); *G01N 2800/52* (2013.01); *G01N 2800/60* (2013.01)

(58) Field of Classification Search
CPC .............................................. G01N 2333/4742
See application file for complete search history.

(56) References Cited

U.S. PATENT DOCUMENTS

| | | | |
|---|---|---|---|
| 2005/0064455 A1* | 3/2005 | Baker | C12Q 1/6886 435/6.14 |
| 2006/0269921 A1 | 11/2006 | Segara et al. | |

FOREIGN PATENT DOCUMENTS

WO    WO 2015/021346 A1    2/2015

OTHER PUBLICATIONS

Yang et al. (Biotechnic & Histochemistry, 2012 87(2): 126-132) (Year: 2012).*
Moffitt Cancer Center (What is Pancreatic Adenocarcinoma? https://moffitt.org/cancers/pancreatic-cancer/types/pancreatic-adenocarcinoma/ Jun. 4, 2020) (Year: 2020).*
Sarbia et al. (Anatomic Pathology 2007 128: 255-259) (Year: 2007).*
Doucet et al. (Cell Reports Jun. 27, 2013 3: 1759-1765) (Year: 2013).*
Escobar-Hoyos, Luisa F. et al., "Keratin-17 Promotes p27KIP1 Nuclear Export and Degradation and Offers Potential Prognostic Utility", Cancer Research (Sep. 1, 2015), vol. 75, No. 17, pp. 3650-3662.
International Search Report dated Jan. 25, 2017 issued in PCT/US2016/059049.
Espina V. et al., "Laser-Capture Microdissection", Nature Protocols 1(2):586-603 (2006).
Gu Y. et al., "Proteomic Analysis of High-Grade Dysplastic Cervical Cells Obtained from ThinPrep Slides Using Laser Capture Microdissection and Mass Spectrometry", Journal of Proteome Research 6(11):4256-4268 (2007).
Ide M. et al., "Keratin 17 Expression Correlates with Tumor Progression and Poor Prognosis in Gastric Adenocarcinoma", Annals of Surgical Oncology 19:3506-3514 (2012).
Ikeda K. et al., "Coordinate Expression of Cytokeratin 8 and Cytokeratin 17 Immunohistochemical Staining in Cervical Intraepithelial Neoplasia and Cervical Squamous Cell Carcinoma: an Immunohistochemical Analysis and Review of the Literature", Gynecologic Oncology 108:598-602 (2008).
Kalantari M. et al., "Laser Capture Microdissection of Cervical Human Papillomavirus Infections: Copy Number of the Virus in Cancerous and Normal Tissue and Heterogeneous DNA Methylation", Virology 390:261-267 (2009).
Maddox P. et al., "Differential Expression of Keratins 10, 17, and 19 in Normal Cervical Epithelium, Cervical Intraepithelial Neoplasia, and Cervical Carcinoma", J Clin Pathol 52:41-46 (1999).
Smedts F. et al., "Basal-Cell Keratins in Cervical Reserve Cells and a Comparison to Their Expression in Cervical Intraepithelial Neoplasia", American Journal of Pathology 140(3):601-612 (Mar. 1992).

(Continued)

*Primary Examiner* — Peter J Reddig
(74) *Attorney, Agent, or Firm* — Scully, Scott, Murphy & Presser, P.C.

(57) ABSTRACT

The instant application relates to methods for determining pancreatic cancer patient outcome and directing treatment to subjects with pancreatic cancer. The present disclosure further provides methods for measuring expression levels of cytokeratin 17 in a subject having pancreatic cancer, such as pancreatic ductal adenocarcinoma, in order to determine the subject's survival rate and clinical outcome.

21 Claims, 9 Drawing Sheets

(9 of 9 Drawing Sheet(s) Filed in Color)

(56) References Cited

OTHER PUBLICATIONS

Van de Rijn M. et al., "Expression of Cytokeratins 17 and 5 Identifies a Group of Breast Carcinomas with Poor Clinical Outcome", American Journal of Pathology 161(6):1991-1996 (Dec. 2002).
Wang Y-F et al., "Overexpression of Keratin 17 is Associated With Poor Prognosis in Epithelial Ovarian Cancer", Tumor Biol. 34:1685-1689 (2013).
U.S. Final Office Action dated Aug. 5, 2020 received in related U.S. Appl. No. 15/804,001.
U.S. non-Final Office Action dated Dec. 15, 2020 received in related U.S. Appl. No. 15/804,001.
Chafin D. et al., "Rapid Two-Temperature Formalin Fixation", PLoS One 8(1):e54138 (Jan. 2013).
Cohen-Kerem R. et al., "Cytokeratin-17 as a Potential Marker for Squamous Cell Carcinoma of the Larynx", Ann Onol Rhino Laryngol 113:821-827 (2004).
Facchinetti M.M. et al., "The Expression of Sphinogosine Kinase-1 in Head and Neck Carcinoma", Cells Tissues Organs 192:314-324 (2010).
Kitamura R. et al., "Association of Cytokeratin 17 Expression With Differentiation in Oral Squamous Cell Carcinoma", J Cancer Res Clin Oncol 138:1299-1310 (2012).
Liu ZB et al., "Expression of CK5/6 and CK17 and its Correlation With Prognosis of Triple-Negative Breast Cancer Patients", Zhonghua Zong Liu Za Zhi 30(8):610-614 (2008), Abstract only.
Makino T. et al., "Cytokeratins 18 and 8 are Poor Prognostic Markers in Patients With Squamous Cell Carcinoma of the Oesophagus", British Journal of Cancer 101:1298-1306 (2009).
Sisk E.A. et al., "Epstein-Barr Virus Detected in a Head and Neck Squamous Cell Carcinoma Cell Line Derived from an Immunocompromised Patient", Arch Otolaryngol Head Neck Surg. 129:1115-1124 (Oct. 2003).
Thompson L.D.R., "Squamous Cell Carcinoma Variants of the Head and Neck", Current Diagnostic Pathology 9:384-396 (2003).
U.S. Final Office Action dated Nov. 30, 2020 received in related U.S. Appl. No. 15/311,611.
Dako Aglient Product Page For Cytokeratin 17 Antibody, (printed Mar. 2018).
Dako Search of CK17 Antibodies (printed Mar. 2018).
U.S. Non-Final Office Action dated Apr. 19, 2021 received in related U.S. Appl. No. 15/311,611.
U.S. Final Office Action dated Jun. 10, 2021 received in related U.S. Appl. No. 15/804,001.

\* cited by examiner

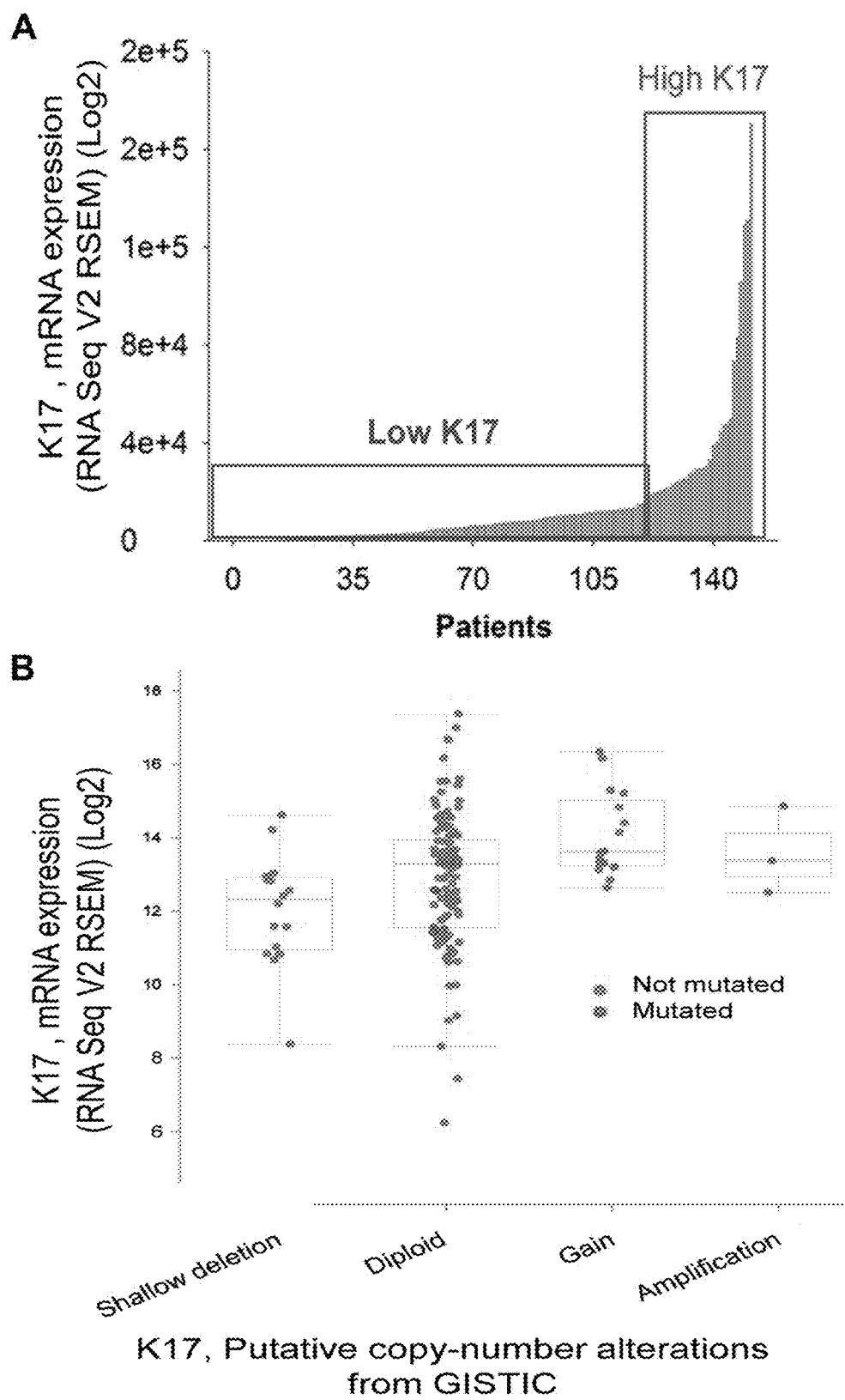
Figure 1A-B

C
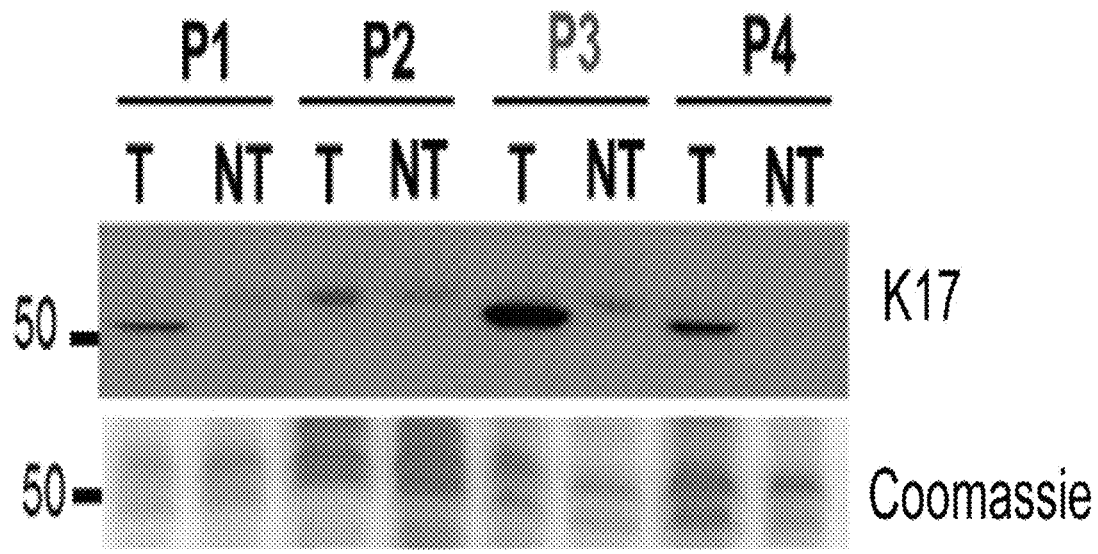
D
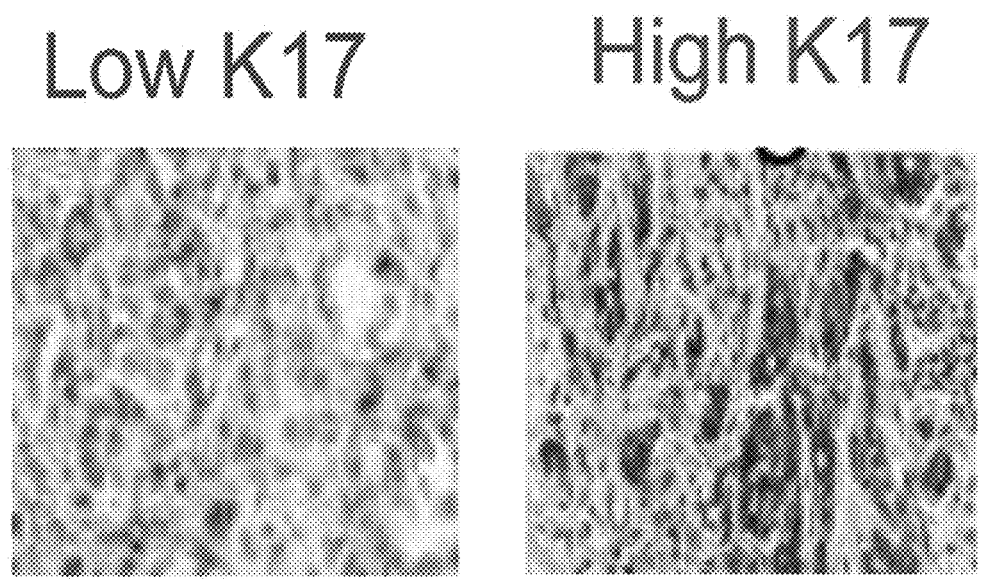
Figure 1C-D

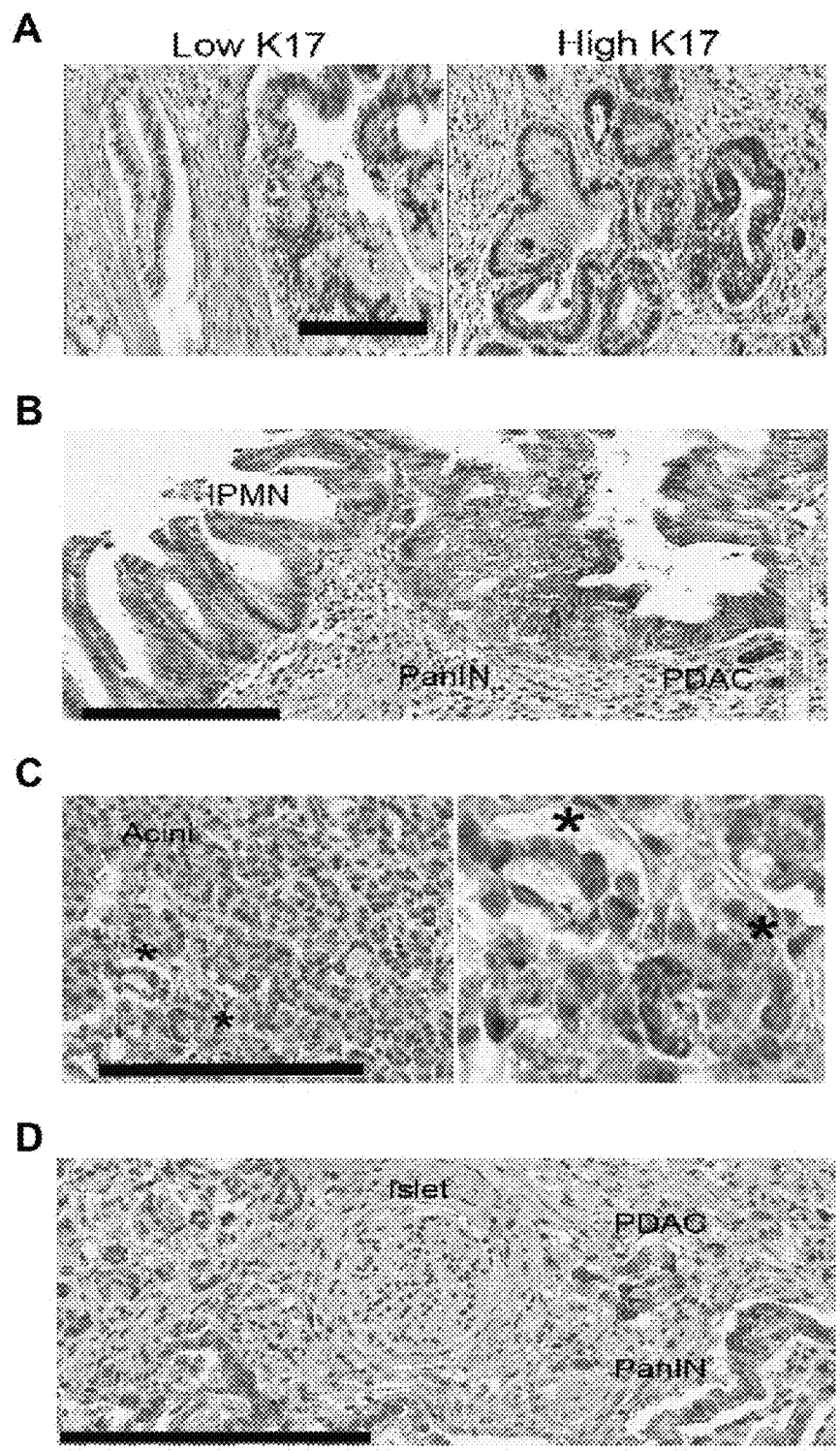
Figure 2A-D

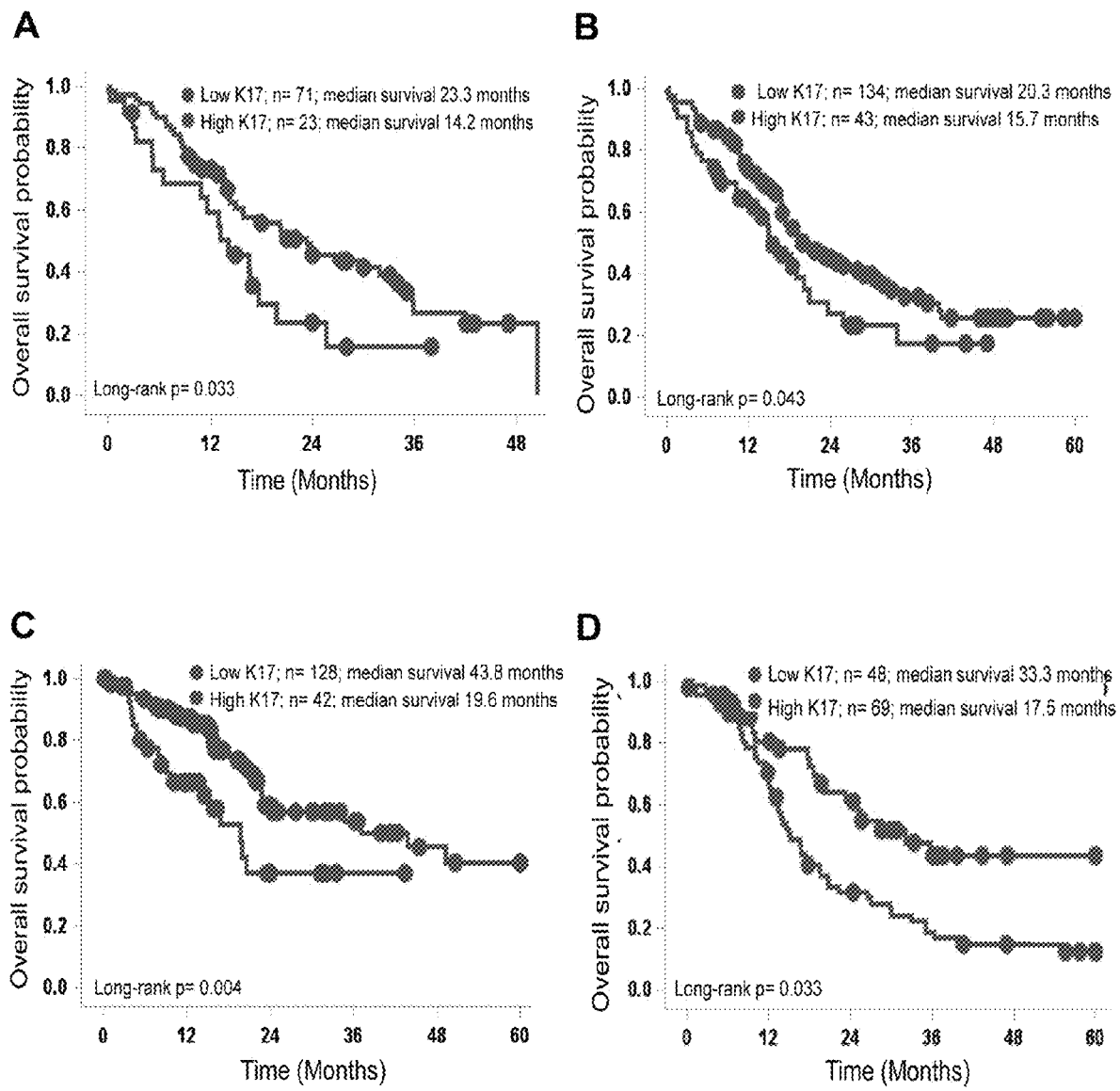
Figure 3A-D

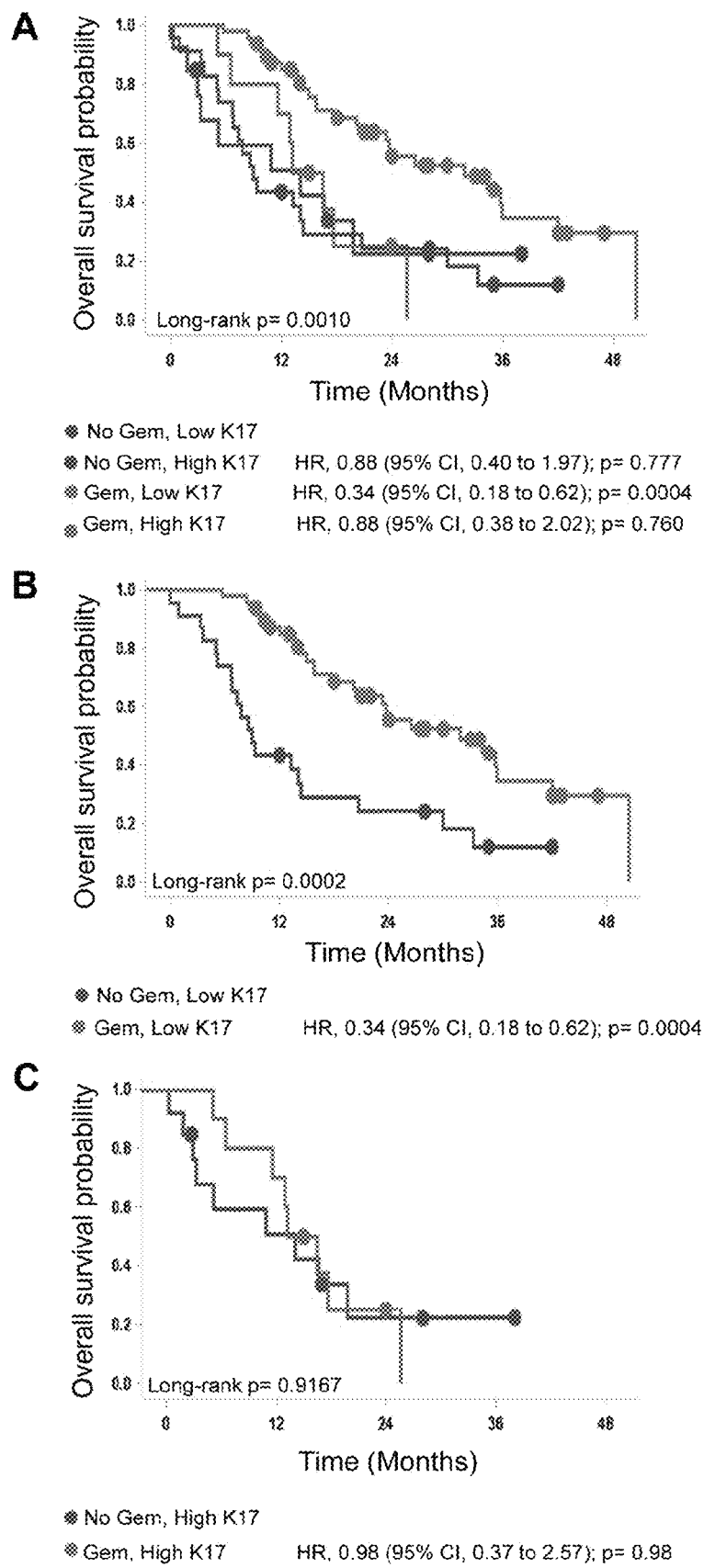
Figure 4A-C

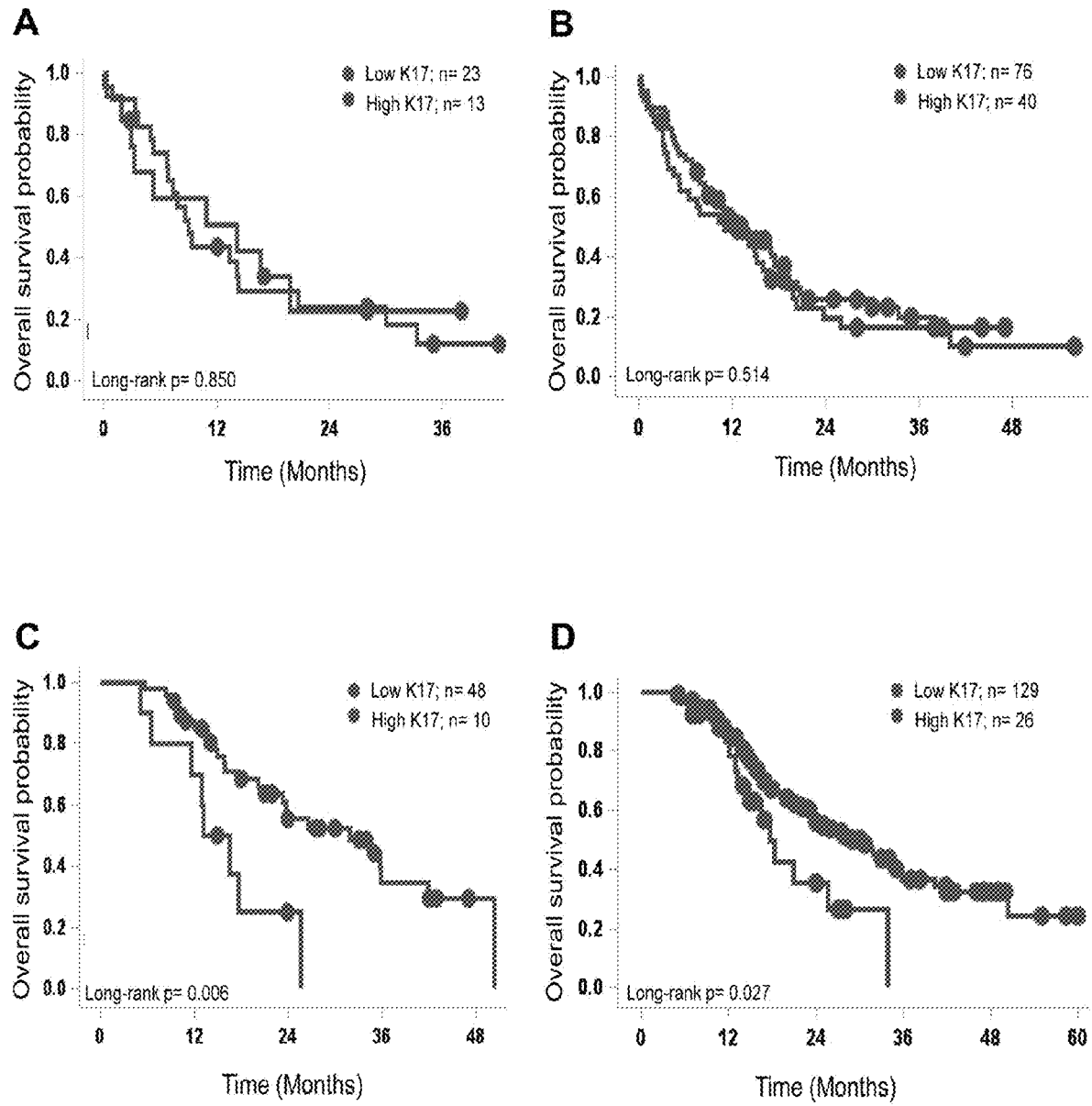
Figure 5A-D

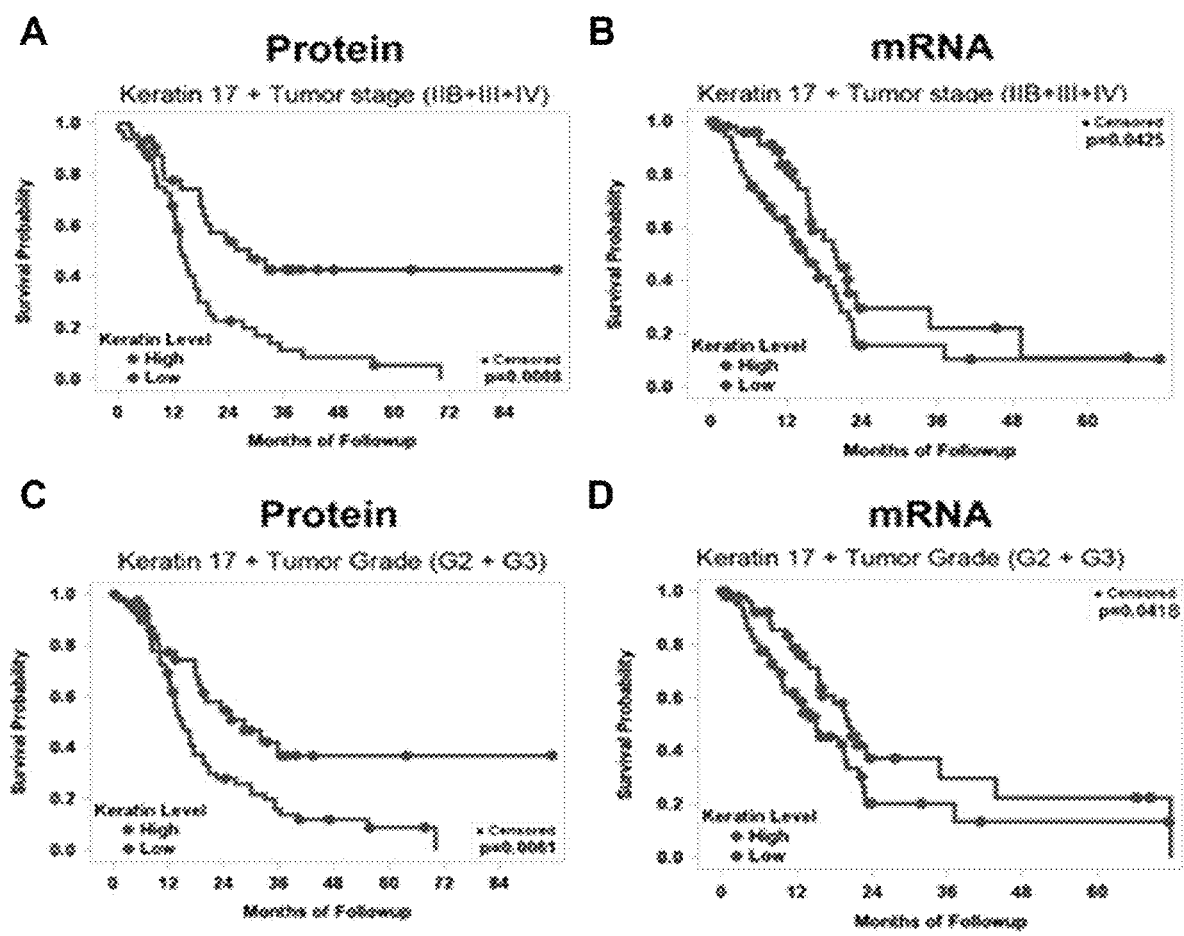
Figure 6A-D

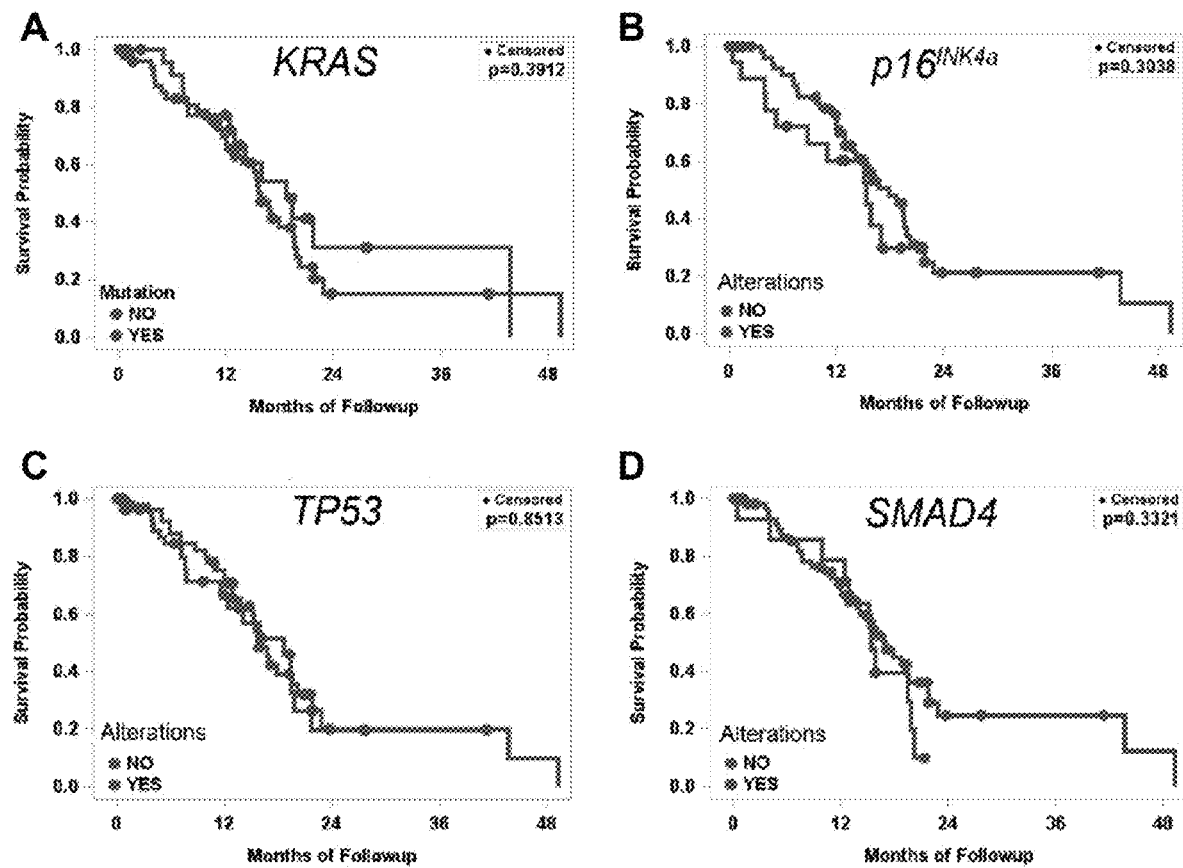
Figure 7A-D

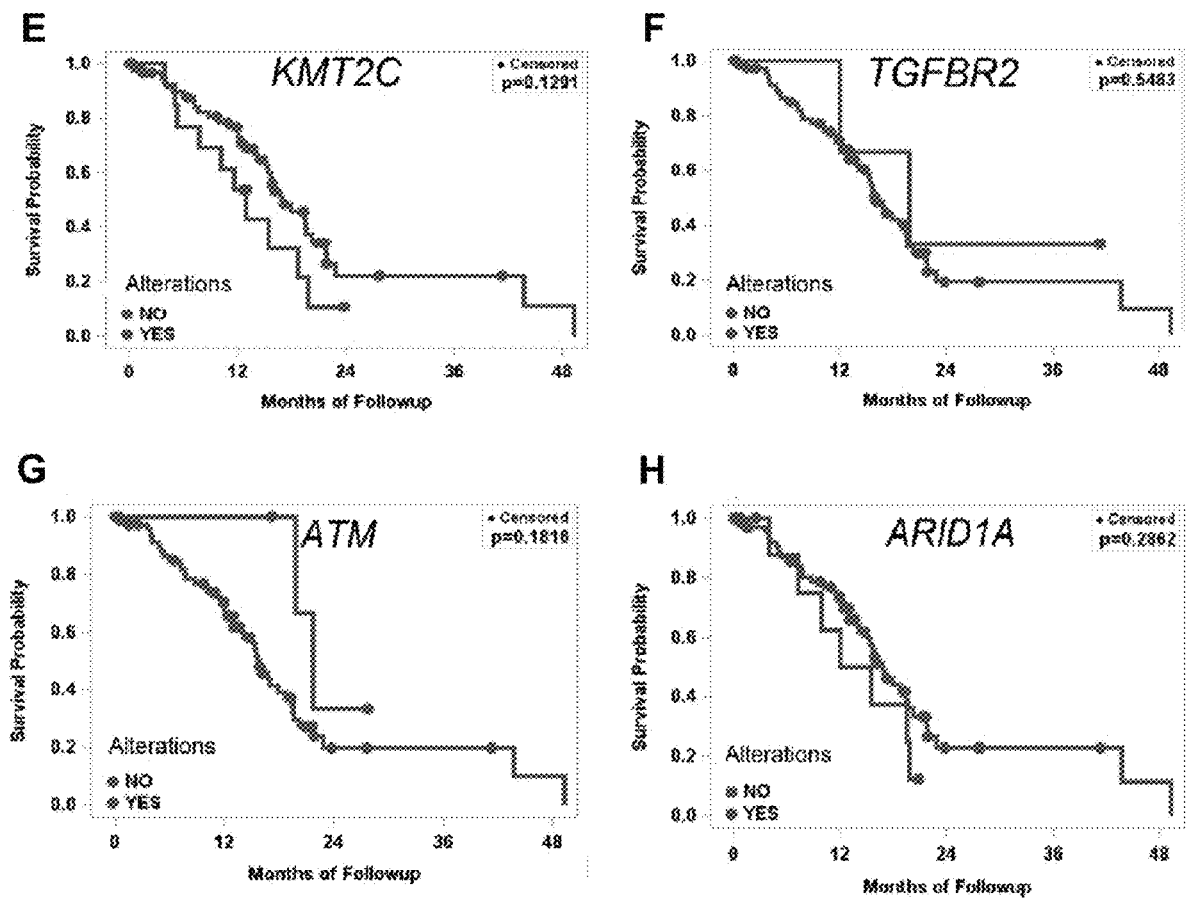
Figure 7E-H

KERATIN 17 AS A PROGNOSTIC MARKER FOR PANCREATIC CANCER

CROSS REFERENCE TO RELATED APPLICATIONS

This application claims priority to U.S. Provisional Application No. 62/248,118, filed on Oct. 29, 2016, the entire contents of which are incorporated herein by reference.

FIELD OF THE DISCLOSURE

The current disclosure relates to methods for determining the likelihood of survival and clinical outcome of subjects having pancreatic cancer based on the detection and expression of certain biomarkers and directing treatment to such subjects. Specifically, the present disclosure provides methods for measuring expression levels of cytokeratin 17 ("K17" or "keratin 17") in a subject having pancreatic cancer, such as pancreatic ductal adenocarcinoma, in order to determine the subject's survival rate and clinical outcome.

BACKGROUND

Pancreatic ductal adenocarcinoma (PDAC) is the fourth leading cause of cancer-related death in the United States, but is projected to rank second by the year 2020. Siegel R L, et al. *CA Cancer J Clin.* 2015; 65:5-29; Rahib L, et al. *Cancer Res.* 2014; 74:2913-21. Even though 5-year survival rate of PDAC patients is only 7% and more than 50% of patients die within the first two years after surgery, long-term survival is achieved by a subset of patients. Siegel R, et al. *CA Cancer J Clin.* 2014; 64:9-29. To date, up to 20% of all pancreatic patients that undergo surgical resection survive beyond five years post surgery and only 10% survive beyond 10 years. Id. Despite the high incidence and low survival rate of PDAC, researches have yet to elucidate the reason behind the variation in PDAC patient survival. Bliss L A, et al. *J Surg Oncol.* 2014; 110:592-8; Brennan M F, et al. *Ann Surg.* 2004; 240:293-8; and Dal Molin M, et al. *Clin Cancer Res.* 2015; 21:1944-50. For example, the current state of art teaches that long term survival in pancreatic cancer is not related to gene mutations commonly associated with various other forms of cancer. Dal Molin M, et al. *Clin Cancer Res.* 2015; 21:1944-50. Currently, patient prognosis is based on tumor stage, histological grade, and lymph node status. Paniccia A, et al. *JAMA Surg.* 2015; 150:701-10. Unfortunately, current prognostic indicators are unable to predict clinical outcome. Brennan M F, et al. *Ann Surg.* 2004; 240:293-8.

Despite continued research directed to pancreatic cancer, the field has failed to identify any independent or interactive prognostic markers associated with known clinical characteristics, PDAC patient outcome and/or genetic profiles. See, e.g., Winter J M, et al. *Ann Surg Oncol.* 2012; 19:169-75; Saukkonen K, et al. *PLoS One.* 2015; 10; and Ballehaninna U K et al. *J Gastrointest Oncol.* 2012; 3:105-19. For example, the pre-operative FDA approved prognostic pancreatic cancer biomarker, CA-19-9, is a carbohydrate antigen that is used to guide patient care. Ballehaninna U K et al. *J Gastrointest Oncol.* 2012; 3:105-19. However, contradictory results regarding the levels for stratification, and limited use this biomarker (i.e., patients with localized disease), render the CA-19-9 biomarker unusable for over two-thirds of PDAC patients. Id.

In view of the foregoing, determination of the factors that mediate survival of pancreatic cancer patients are sorely needed to direct treatment and improve clinical outcome. Consequently, the present disclosure identifies, for the first time, that K17 over expression in a subject is a clear indicator of pancreatic cancer metastasis, patient survival and clinical outcome.

SUMMARY OF THE DISCLOSURE

Without being bound by any one theory, the present disclosure is based on the inventor's determination that the amount of keratin 17 in samples obtained from subjects diagnosed with pancreatic cancer can be used to determine patient survival rate, a subject's response to surgical resection and treatment outcome. More specifically, detection of increased amounts of K17 protein expression by immunohistochemistry, or detection of increased amounts K17 RNA expression in a sample obtained from a subject diagnosed with pancreatic cancer (e.g., PDAC) correlate with decreased survival probability when compared to subjects with control (low or normal) amounts of K17. Additionally, elevated K17 protein expression and/or RNA expression in a sample was found to be a clear indicator for determining a subject's response to surgical resection and cancer treatment.

Therefore, in one aspect of the present disclosure an increased amount of K17 expression in subjects with PDAC is detected. In some embodiments, the amount (i.e., level) of K17 expression is detected by obtaining a biological sample from a subject and contacting the sample with an antibody that binds to K17. In other embodiments of the present disclosure, the level of K17 expression is detected by obtaining a biological sample from a subject and measuring the amount of K17 RNA in the sample (i.e., RNA quantification). In specific embodiments, an increased level of K17 expression is present in a sample when the level of keratin 17 expression in the sample is greater than the level of keratin 17 expression detected in a control sample. In one embodiment, an increased level of K17 expression is shown by an increase in the amount of K17 detected in a sample that is at least 11-times greater than that expressed in a control sample. In a specific embodiment, an increased level of K17 expression in a sample is shown when about a 10-times to about a 12-times increase in keratin 17 expression is detected when compared to the amount of K17 detected in a control sample.

In other embodiments, an increased level of K17 expression is shown by a 1-fold to 50-fold increase in K17 expression compared to a control or normal level of K17 expression. In other embodiments, an increased level of K17 expression in sample is shown by a 1-fold to 30-fold, 1-fold to 25-fold, 1-fold to 20-fold, 1-fold to 15-fold, 5-fold to 15-fold, 10-fold to 15-fold or 11-fold to 13-fold increase in K17 expression compared to a control or normal level of K17 expression.

In certain embodiments, when an increased level of K17 expression is detected in a sample obtained from a subject that has been diagnosed with pancreatic cancer, such as PDAC, the increase in the amount of K17 expression detected indicates a shorter survival time of the subject when compared to a subject having PDAC that expresses control levels of K17. In some embodiments, the increase in K17 expression detected in a sample that corresponds to a reduction in survival time of the subject is shown when the amount of K17 in the sample is greater than the level of keratin 17 expression detected in a control sample. In one embodiment, an increased level of K17 expression is shown by an increase in the amount of K17 detected in a sample that is at least 11-times greater than that expressed in a control sample. In a specific embodiment, an increased level of K17 expression in a sample is shown when about a 10-times to about a 12-times increase in keratin 17 expression is detected when compared to the amount of K17 detected in a control sample.

In some embodiments, the increase in K17 expression detected in a sample that corresponds to a reduction in survival time of the subject is 1-fold to 20-fold, 5-fold to 20-fold, 5-fold to 15-fold, 10-fold to 20-fold, 5-fold to 15-fold, 10-fold to 15-fold or 11-fold to 13-fold increase in K17 expression compared to a control or normal level of K17 expression. In other embodiments, the increase in K17 expression detected in a sample that corresponds to a reduction in survival time of the subject is about a 3-fold or about a 5-fold increase in keratin 17 expression compared to the amount of K17 detected in a control sample.

In some embodiments of the present disclosure, an increased level of K17 expression in a sample identifies the subject as a patient that will not respond positively to surgical resection and/or adjuvant therapy (e.g., treatment with chemotherapy), when compared to a subject exhibiting low or control levels of K17 expression. As such, patients exhibiting increased amounts of keratin 17 should not receive treatment by surgical resection and chemotherapy. In certain embodiments, a subject having an increased level of K17 expression will not respond positively to chemotherapy, such as gemcitabine. In certain embodiments, a subject having an increased level of K17 expression will not respond positively to surgical resection. In one embodiment, an increased level of K17 expression is shown by an increase in the amount of K17 detected in a sample that is at least 11-times greater than that expressed in a control sample. In certain embodiments, an increased level of K17 expression that indicates that the subject will not respond positively to surgical resection and/or chemotherapy, is shown by the detection of K17 expression levels that is from 11-times to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that indicates that the subject will not respond positively to surgical resection and/or chemotherapy is shown by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In one embodiment, the increased level of K17 expression that indicates that the subject should not receive surgical resection and/or chemotherapy is shown by the detection of K17 expression that is about 11-times greater than the amount of K17 expression detected in a PDAC sample having low or control levels of K17.

In some embodiments, the increase in K17 expression detected in a sample that corresponds to subject's inability to respond positively to chemotherapy and/or surgical resection is about 1-fold to 20-fold, 5-fold to 20-fold, 5-fold to 15-fold, 10-fold to 20-fold, 5-fold to 15-fold, 10-fold to 15-fold or 11-fold to 13-fold increase in K17 expression compared to a control or normal level of K17 expression. In other embodiments, the increase in K17 expression detected in a sample that corresponds to subject's inability to respond positively to chemotherapy and/or surgical resection is about a 3-fold or about a 5-fold increase in keratin 17 expression compared to the amount of K17 detected in a control sample.

BRIEF DESCRIPTION OF THE DRAWINGS AND TABLES

The patent or application file contains at least one drawing executed in color. Copies of this paper or patent application publication with color drawing(s) will be provided by the Office upon request and payment of the necessary fee.

FIG. 1A-D. Keratin 17 protein and mRNA is detected at different levels in pancreatic cancer. A. K17 mRNA expression levels detected in samples obtained from patients diagnosed with PDAC containing increased (high) and control (low) levels of K17 PDACs (scale bar, 200 µm). B. Changes in the amount of K17 mRNA expression detected in PDAC samples are not the result of changes in K17-gene copy number or K17-gene mutations (frequency <2%). K17 mRNA expression based on putative copy-number alterations from Genomic Identification of Significant Targets in Cancer (GISTIC) algorithm. Mutated, nonsynonymous mutation; Diploid, two alleles present; Gain, low-level gene amplification event; Shallow Deletion, low-level gene deletions event; Amplification, high-level gene amplification event; Normal, no mutation or CNA present. C. K17 protein expression as detected by Western blotting is increased in pancreatic cancer patients compared to the control samples, as shown by for representative PDAC samples (P1-P4). PDAC tumor samples (T) show a clear increase in the amount of K17 protein when compared to non-tumor (NT) matched samples from each PDAC patient (P). D. K17 protein expression detection in representative PDAC samples as determined by quantitative immunohistochemical staining with a mouse monoclonal antibody that binds to K17. Representative PDAC sections stained for K17 were classified as having normal or control (low) K17 expression levels or increased (high) K17 expression levels based on PathSQ quantification.

FIG. 2A-D. K17 protein detection by immunohistochemical analysis in different pancreatic tissue samples obtained from subjects diagnosed with PDAC. A. K17 protein detection in patients with PDAC that exhibit normal or control (low) K17 expression levels or increased (high) K17 expression levels. The samples shown exhibit increased K17 expression in pancreatic ductal intraepithelial neoplasias (PanINs) tissue samples taken from PDAC patients with high K17 expressions levels and low K17 expression levels are detected in PanIN samples taken from PDAC patients exhibiting control levels of K17. K17 immunoreactivity in intraductal papillary mucinous neoplasm (IPMN) (C), normal acinar cells and acinar-to-ductal metaplasia (*), (D) and in islet cells accompanied by PanIN and PDAC). Scale bars 200 µm.

FIG. 3A-D. Increased expression of keratin 17 is a negative prognostic marker in Pancreatic Ductal Adenocarcinomas. On the basis of K17 expression, PDACs were defined as low or high-K17 based on the $76^{th}$ percentile of expression. This cut-off value was used in all four independent cohorts of PDAC patients (i.e., A, B, C, D). Kaplan-Meier curves depicting overall survival probabilities between low and high K17 expressing PDAC patients for four independent cohorts of PDAC cases. (A) First PDAC patient cohort; (B) second PDAC patient cohort; (C) third PDAC patient cohort from The Cancer Genome Atlas (TCGA) and the (D) fourth PDAC patient cohort from the Department of Pathology at Stony Brook University.

Cohorts shown in A-C depict K17 mRNA levels, while patient cohort D depicts K17 protein levels.

FIGS. 4A-C: Low keratin 17 expression is associated with outcome after Gemcitabine treatment in Pancreatic Ductal Adenocarcinomas. A. Patient samples exhibiting K17 expression levels were separated based on whether or not a patient received chemotherapy, Gemcitabine (Gem), or were not treated with gemcitabine (No Gem) as an adjuvant therapy. The difference in overall survival (HR) in the low and high K17 expression samples in the No Gem cohort was not statistically significant (dark blue and red curves). B. Patients with low-K17 expression levels exhibited significantly increased overall survival after adjuvant treatment with Gem (light blue curve), when compared to compared patients exhibiting low-K17 expression levels who did not receive Gem (dark blue curve). C. The overall survival of Gem-treated patients for which increased K17 expression levels (High K17) were detected in tumors (pink curve) was not significantly different from the overall survival of patients for which increased K17 expression levels were detected in tumors who did not received Gem. A multivariable Cox model was evaluated that included the prognostic factors as adjusting variables, K17 status, treatment group, and a K17 status and treatment group interaction group term. In this model, the interaction term value was very near significant (P=0.06). B and C show the effect of the interaction on Gem and overall survival of a subject. These results show that low or control amounts of K17 expression in PDACs provide a means of predicting benefit to a patient from adjuvant chemotherapy.

FIGS. 5A-D. Keratin 17 expression is associated with decreased response to Gemcitabine treatment in Pancreatic Ductal Adenocarcinomas. Patient samples from two separate cohorts (A and C; B and D) exhibiting K17 expression levels were separated based on whether or not a patient received chemotherapy, Gemcitabine (Gem), or were not treated with gemcitabine (No Gem) as an adjuvant therapy. The difference in overall survival in the control (low) and increased (high) K17 cases in patients across both cohorts that were not treated with gemcitabine was not statistically significant (A and B). However, patients with control (low-K17) keratin 17 expression levels exhibited significantly increases in overall survival with Gem, compared to subjects for which increased levels of K17 was detected who received chemotherapy (C and D)

FIG. 6A-D. Stratification of survival in PDACs based on K17 expression level detected. A-D. Kaplan-Meier survival curves depicting the overall survival of PDAC patients integrating K17 status and in metastatic disease, i.e., tumor stage (A and B), and in poorly differentiated tumors, i.e., tumor grade (C and D). Cohorts shown in A and C depict K17 mRNA levels detected in a samples B and C depict K17 protein levels detected in PDAC subjects.

FIG. 7A-H. Stratification of survival in PDACs based on K17 status and Mutations. A-H, Kaplan-Meier curves depicting the overall survival of PDAC patients integrating K17 expression levels detected (low, high) and mutation status (wild-type or altered gene expression). P values were calculated using the log-rank test. These results suggest that somatic mutation profiles in PDAC patients are not the primary determinant of long-term survival in this disease. Hence, patient survival and clinical outcome is independent of genetic mutation.

Table 1. Univariate and multivariate analyses of overall survival on each PDAC patient Cohort tested in FIG. 3A-D.

n=number of subjects for which samples K17 expression levels were measured for each cohort. CI: Confidence interval.

Table 2. Prognostic value of gene mutations (univariate) and Interaction with K17 status in overall survival. CI: Confidence interval. Bold characters represent significant results for Chi-square. † Marginally significant results for Chi-square.

Table 3. Bootstrap and Jackknife Validation Results for the Effect of Changing Keratin 17 from Low to High. BS: bootstrap; JK: jackknife; CI: Confidence interval; HR: hazard ratio. IA/IB/IIA: Tumor stages—localized disease; IIB/Ill/IV: Tumor stages—metastatic disease. G1: Well differentiated; G2: Moderately differentiated; G3, Poorly differentiated. Cancer is still within the pancreas and is <2 cm (T1) or >2 cm (T2). The cancer has grown outside the pancreas into surrounding tissues but not into major blood vessels or nerves (T3), or into nearby large blood vessels or nerves (T4). N0: Lymph node negative; N1: Lymph node positive. Note: all original estimated keratin 17 hazard ratios (see Table 1) fall within the corresponding bootstrap 95% confidence interval and low and high jackknife results. Bold characters represent statistically significant hazard ratio results (for the Chi-square test) in the stratified model (see Table 1) and validation of these significant results, in all cases, from the bootstrap and jackknife analyses. * denotes modeled data.

DETAILED DESCRIPTION OF THE DISCLOSURE

Pancreatic cancer, specifically pancreatic ductal adenocarcinoma, is a unique and deadly form of cancer as evidenced by its dismal survival rate and high variation in patient survival time. Without being limited by any particular theory, the present disclosure is based on the new recognition that the detection of increased amounts of keratin 17 proteins and/or mRNA expression in a patient sample can be used to determine patient prognosis for subject's diagnosed with pancreatic ductal adenocarcinomas.

The present disclosure demonstrates that K17 expression is a prognostic marker that highlights biologically aggressive tumors with similar clinicopathologic features, adding complementary survival information to the current standard-of-care prognosis model. Specifically, the present disclosure demonstrates that pancreatic cancer patients with metastatic disease, having tumors expressing increased levels of K17 have an increased risk of not responding to surgical resection and adjuvant therapy and dying from this disease within five years, when compared to pancreatic cancer patients expressing low or control levels K17.

As such, in the present disclosure increases in K17 expression levels have been observed in PDAC samples obtained from patients relative to other cancerous samples or non-cancerous control samples, which have been correlated with a reduced incidence of survival and/or a negative treatment outcome. Hence, in certain embodiments of the instant disclosure when an increased level of K17 expression is detected in a sample obtained from a subject, the subject is likely to have a reduced likelihood of survival and/or negative treatment outcome when compared to a subject diagnosed with PDAC that does not have an increase in K17 expression over that of normal K17 expression levels or the amount of K17 expression detected in a control sample.

Taken together, the current disclosure reveals that increased K17 expression is a critical event in the development and progression of pancreatic cancer and that K17 protein detection can be measured and expression (e.g., binding) levels can be used as a prognostic indicator of PDAC patient survival and clinical outcome.

Terminology

The term "peptide" or "protein" as used in the current disclosure refers to a linear series of amino acid residues linked to one another by peptide bonds. In one embodiment, the protein is keratin 17.

The term "nucleic acid" as used herein refers to one or more nucleotide bases of any kind, including single- or double-stranded forms. In one aspect of the current disclosure a nucleic acid is DNA and in another aspect the nucleic acid is RNA. In practicing the methods of the current disclosure, nucleic acid analyzed (e.g., K17 RNA) by the present method is originated from one or more samples.

The term "keratin 17", "K17" or "KRT17" as used herein refers to the human cytokeratin, keratin, type II cytoskeletal 4 gene located on chromosome 17, as set forth in accession number NG_008625 or a product thereof, which encodes the type I intermediate filament chain keratin 17 mRNA and protein. Included within the intended meaning of K17 are mRNA transcripts of the keratin 17 cDNA sequence, as set forth in accession number NM_000422, and proteins translated therefrom including for example, the keratin, type 1 cytoskeletal protein, 17 as set forth in accession number NP_000413 or homologs thereof.

The phrase "subject", or "patient" in its most general application refers to any mammal. In one embodiment, the subject is a candidate for cancer diagnosis or an individual with pancreatic cancer, such as pancreatic ductal adenocarcinoma (PDAC) or the presence of a pre-cancerous lesion, such as pancreatic ductal intraepithelial neoplasias (PanINs) or intraductal papillary mucinous neoplasm (IPMN). In certain embodiments, the subject has been diagnosed with PDAC and the subject is a candidate for treatment thereof. The methods of the current disclosure can be practiced on any mammalian subject that has a risk of developing pancreatic cancer or has been diagnosed with pancreatic cancer or a precursor thereof. Particularly, the methods described herein are most useful when practiced on humans diagnosed with pancreatic cancer.

A "biological sample," "test sample" or "sample(s)" as used in the instant disclosure can be obtained in any manner known to a skilled artisan. Samples for use in the present methods can be derived from any part of the pancreas of a subject, including whole blood, tissue, lymph node or a combination thereof. In certain embodiments, the sample is a tissue biopsy, fresh tissue or live tissue extracted from a subject. In one embodiment, the sample is a tissue sample obtained from the pancreas of a subject. In other embodiments, the sample is processed prior to use in the disclosed methods. For example, a formalin-fixed, paraffin-embedded tissue sample isolated from a subject are useful in the methods of the current disclosure because formalin fixation and paraffin embedding is beneficial for the histologic preservation and diagnosis of clinical tissue specimens, and formalin-fixed paraffin-embedded tissues are more readily available in large amounts than fresh or frozen tissues. In a preferred embodiment, the sample is obtained from a subject diagnosed with pancreatic cancer, such as PDAC.

A "control sample" or "normal sample" as used herein is a sample which does not exhibit increased K17 expression levels. In certain embodiments, a control sample does not contain cancerous cells (e.g., benign tissue components including, but not limited to, normal acinar cells). In another embodiment, a control or normal sample is a sample from benign or cancerous pancreatic tissue that does not exhibit elevated K17 expression levels when compared to non-cancerous pancreatic tissue samples. Non-limiting examples of control samples for use in the current disclosure include non-cancerous tissue extracts, surgical margins extracted from the subject, isolated cells known to have normal or reduced amounts of K17, or samples obtained from other healthy individuals. In one embodiment, the control sample of the present disclosure is pancreatic tissue obtained from another subject diagnosed with PDAC having low or normal levels of K17.

The term "increase", "high", "greater" or "elevated", as used herein means an amount that is at least more than the relative amount of an entity identified, measured or analyzed in a control sample. Non-limiting examples include, but are not limited to, a 5-10%, 10-20% increase in K17 expression detected over that detected in a control sample, or at least 20%, 30%, 40%, 50%, 60%, 70%, 80%, 90%, 100%, 200%, 1000% or greater increase over that of a control sample, or at least a 11-times or greater increase in expression relative to the entity being analyzing in the control sample.

The term "decrease", "low" or "reduced", as used herein means an amount least less than the relative amount of an entity identified, measured or analyzed in a control sample. Non-limiting examples, include but are not limited to, 5-10%, 10-20% decrease in K17 expression detected compared to that of a control sample, or at least 20%, 30%, 40%, 50%, 60%, 70%, 80%, 90%, 100%, 200% or greater decrease when compared to that of a control sample, or at least a 11-times or greater reduction in expression relative to the entity being analyzing in the control sample.

An "increased level of K17 expression" or "increased amount of K17 expression" can be used interchangeably. As used in the current disclosure these terms shall mean an increase in the amount of K17 protein or peptide fragments thereof, or K17 RNA present in a cell, organism or sample as compared to a control or normal level of K17 expression.

Prognostic Methods

Detection of increased K17 protein expression by immunohistochemistry, or detection of increased K17 RNA expression in a sample obtained from a patient diagnosed with pancreatic cancer correlate with decreased survival time when compared to subjects with low or normal K17 levels. Elevated K17 protein expression and/or RNA expression in a pancreatic sample obtained from a subject diagnosed with pancreatic cancer was found to be a clear indicator for determining a subject's response to surgical resection and cancer treatment. In view of the foregoing, the role of keratin 17 was characterized as a prognostic marker for pancreatic cancer.

As shown in FIGS. 3-5 of the present disclosure, elevated expression of K17 in a subject diagnosed with PDAC indicates that the subject will have a reduced likelihood of survival and/or a negative treatment outcome when compared to a subject diagnosed with pancreatic cancer that does not exhibit an increase in K17 expression. See, also, Tables 1 and 3.

In view of the foregoing, one aspect of the present disclosure provides methods for determining the likelihood of survival of a subject having pancreatic cancer, which includes obtaining a sample from a subject, detecting the level of K17 expression in the sample; and, optionally, further evaluating the K17 expression level in the sample obtained by comparing the level of K17 expression detected to the level of K17 expression detected in cancerous samples obtained from other subjects and/or a control sample having low or normal levels of K17.

In certain embodiments, a biological sample is obtained from the subject in question, i.e., a subject or patient diagnosed with pancreatic cancer or a precursor thereof. A biological sample, which can be used in accordance with the present methods, may be collected by a variety of means known to those of ordinary skill in the art. Non-limiting examples of sample collection techniques include; fine needle aspiration, surgical excision, endoscopic biopsy, excisional biopsy, incisional biopsy, fine needle biopsy, punch biopsy, shave biopsy and skin biopsy. Additionally, K17 expression can be detected from cancer or tumor tissue or from other body fluid samples such as whole blood (or the plasma or serum fractions thereof) or lymphatic tissue. In certain embodiments, the sample obtained from a subject is used directly without any preliminary treatments or processing, such as formalin-fixing, flash freezing, or paraffin embedding. In a specific embodiment, a biological sample can be obtained from a subject and processed by formalin treating and embedding the formalin-fixed sample in paraffin, and stored prior to evaluation by the instant methods.

In certain embodiments, after a suitable biological sample is obtained, the level of K17 expression in the sample can be determined using various techniques known by those of ordinary skill in the art. In specific embodiments of the current disclosure, K17 expression levels is detected by a process selected from: immunohistochemistry (IHC), microscopy, q-RT-PCR, northern blotting, western blotting, enzyme-linked immunosorbent assays (ELISA), microarray analysis, or RT-PCR.

In one embodiment, immunohistochemical analysis of keratin 17 expression levels is conducted on formalin-fixed, paraffin-embedded samples. Here, pancreatic cancer tissue samples (e.g., PDAC) or samples from a pre-cancerous lesion, such as pancreatic ductal intraepithelial neoplasias (PanINs) or intraductal papillary mucinous neoplasm (IPMN) are stained with hematoxylin and eosin and dissected by laser capture microscopy. The formalin-fixed, paraffin-embedded samples or a portion thereof are then incubated in 50 mM Ammonium Bicarbonate with protease cocktails to facilitate the reverse of protein cross-linking. The sample(s) can then be further processed by homogenization in urea. The amount of K17 can then be measured by any suitable method known to one of skill in the art.

In a specific embodiment, K17 protein detection is carried out via tissue microarray. For example, tissue obtained from a pancreatic cancer (e.g., PDAC) sample is be obtained from paraffin blocks and placed into tissue microarray blocks. In certain embodiments, other sources of tissue samples can be used as control samples including, but not limited to, commercial tissue microarray samples, such as those obtained from HISTO-Array™, non-cancerous pancreatic tissue or pancreatic tumor tissue samples with known control K17 expression levels. Tissue microarray slides for use in the current methods can then be processed, i.e., deparaffinized in xylene and rehydrated using an alcohol.

In certain embodiments, a sample can then be further processed by: incubation with a citrate buffer, applying hydrogen peroxide to block endogenous peroxidase, or by treating the sample with serum to block non-specific binding (e.g., bovine, donkey, human or horse serum). The pancreatic tissue samples can then be further incubated with a primary antibody against K17. More specifically, the human K17 antigen can be detected by mouse monoclonal-[E3] anti-human K17 antibody or by the rabbit monoclonal [EP1623] anti-human K17 antibody that specifically bind to the human K17 antigen. After incubation with the primary antibody, samples are processed by an indirect avidin-biotin-based immunoperoxidase method using biotinylated secondary antibodies, developed, and counter-stained with hematoxylin. Slides can then be analyzed for K17 expression using microscopy (e.g., fluorescent microscopy or light microscopy), as depicted in FIGS. 1D and 2A-D.

In other embodiments, polyclonal antibodies against human K17, a monoclonal antibody or polyclonal antibody against a mammalian K17 protein domain or epitope thereof.

In certain specific embodiments, keratin17 expression is quantified by PathSQ method, a manual semi-quantitative scoring system, which quantifies the percentage of strongly stained cells, blinded to corresponding clinical data. In yet another embodiment, slides can be scored by the National Institutes of Health ImageJ 1.46, Java-based image processor software using the DAB-Hematoxylin (DAB-H) color deconvolution plugin. See Schneider C A, et al., *Nat methods*. (2012) 9:671-5.

In another embodiment, K17 expression can be determined using enzyme-linked immunosorbent assays (ELISA). For example, a monoclonal antibody specific for K17, e.g., mouse monoclonal-[E3] anti-human K17 antibody, is added to the wells of microtiter strips or plates. Pancreatic cancer samples obtained from a subject, and a control sample containing control or low K17 protein expression levels are provided to separate wells. The samples are then incubated to allow the K17 protein antigen to bind the immobilized (capture) K17 antibody. The samples are then subjected to a washing with a buffer solution and subsequently treated with a detection antibody capable of binding by binding to the K17 protein captured during the first incubation. In certain embodiments, after removal of excess detection antibody, labeled antibody (e.g., anti-rabbit IgG-HRP) is added, which binds to the detection antibody to complete complex formation. After a third incubation and washing to remove all the excess labeled antibody, a substrate solution is added, which is acted upon by the bound enzyme to produce color. The intensity of this colored product is directly proportional to the concentration of total K17 protein present in the original sample. The amount of K17 protein present in a sample can then be determined by reading the absorbance of the sample and comparing to the control wells, and plotting the absorbance against control K17 expression levels using software known by those of ordinary skill in the art.

In yet another embodiment, K17 expression can be measured using reverse transcriptase PCR (RT-PCR) or quantitative-RT-PCR. More specifically, total RNA can be extracted from a pancreatic cancer sample by using a Trizol reagent. Reverse transcriptase PCR can then be performed using methods know by one of ordinary skill in the art. For example, RNA can be used as a template for cDNA synthesis and cDNA templates can then be mixed with gene-specific primers (i.e., forward, 5'-3' primer sequence and reverse 3'-5' sequence) for K17. Probe sequences for detection can also be added (e.g., Taqman or SYBR Green) using methods known by those of ordinary skill in the art. Real-time quantitative PCR can then be carried out on each sample and the data obtained can be normalized to control levels of K17, as set forth in a control sample. See, for example, Schmittgen, and Livak, *Nature protocols* (2008) 3: 1101-1108. mRNA K17 scoring and the threshold for increased K17 expression in a sample was defined to be at the 76th percentile. More specifically, the score and amount of K17 mRNA in a sample is dependent on the distribution of the K17 expression within a cohort of patients. This method ensures continuity across cohorts and samples that are obtained using, for example, different RNA sequencing methods, and differing methods for the enrichment of epithelial cells.

In a specific embodiment, samples mounted on slides and stained with K17 antibodies can be analyzed and scored by the National Institutes of Health ImageJ 1.46 (see Schneider C A, et al., *Nat methods*. (2012) 9:671-5) Java-based image processor software using the DAB-Hematoxylin (DAB-H) color deconvolution plugin (see Ruifrok A C, Johnston D A. *Anal Quant Cytol Histol*. (2001) 23:291-9) and/or by a manual semi-quantitative scoring system, which quantifies the percentage of strong-positively stained cells blinded to corresponding clinical data (PathSQ). More specifically, for protein expression K17 expression was quantified by a PathSQ scoring system, from 0 to 100. Whereby the PathSQ score per sample (i.e., patient) is dependent of the percentage of malignant cells stained for K17 in a particular sample from the subject.

In preferred embodiments, the level of K17 expression in a sample is determined by determining an ImageJ score and/or a PathSQ score for a subset of patients and choosing an appropriate level of K17 expression according to the lowest Akaike's information criteria in view of a Cox proportional-hazard regression model. In certain embodiments, a patient sample exhibiting an increased (high) level of K17 expression is shown by a PathSQ score of at least 25%. In contrast, a PathSQ score of less than 25% corresponds to a control or low level of K17 expression in a sample.

Regardless of the method used to detect K17 expression in a PDAC sample obtained from a subject, an increased amount of K17 expression in the sample corresponding to a reduced incidence of survival beyond 2 and/or 5 years when compared to a control or standard incidence of survival, is indicated by the detection of K17 expression levels that are at least greater than that of a control sample. In one embodiment, an increased level of K17 expression is shown by an increase in the amount of K17 detected in a sample that is at least 1-times, 2-times, 3-times, 4-times, 5-times, 6-times, 7-times, 8-times, 9-times, 10-times, 11-times, 12-times, 13-times, 14-times or 15-times greater than that expressed in a control sample. In certain embodiments, an increased level of K17 expression that corresponds with a reduced incidence of survival beyond 2 and/or 5 years when compared to a control or standard incidence of survival, is indicated by the detection of K17 expression levels that is from 1-time to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that corresponds with a reduced incidence of survival beyond 2 and/or 5 years when compared to a control or standard incidence of survival, is indicated by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In specific embodiments, the expression an increased level of K17 expression that corresponds with a reduced incidence of survival beyond 2 and/or 5 years when compared to a control or standard incidence of survival, is indicated by the detection of K17 expression levels that is from 5-times to 15-times, 7-times to 14-times, 8-times to 13-times, 9-times to 12-times, 10-times to 12-times or 10-times to 11-times greater than that expressed in a PDAC sample having low or control levels of K17. In one embodiment, the increased level of K17 expression that corresponds with a reduced incidence of survival beyond 2 and/or 5 years when compared to a control or standard incidence of survival, is indicated by the detection of K17 expression at a level that is from 11-times greater than the amount of K17 expression detected in a PDAC sample having low or control levels of K17.

In certain embodiments, an increased level of K17 expression that corresponds with a reduced incidence of survival beyond 2 years when compared to a control or standard incidence of survival, is indicated by the detection of K17 expression levels that is from 1-time to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that corresponds with a reduced incidence of survival beyond 2 years when compared to a control or standard incidence of survival, is indicated by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In specific embodiments, the expression an increased level of K17 expression that corresponds with a reduced incidence of survival beyond 2 years when compared to a control or standard incidence of survival, is indicated by the detection of K17 expression levels that is from 5-times to 15-times, 7-times to 14-times, 8-times to 13-times, 9-times to 12-times, 10-times to 12-times or 10-times to 11-times greater than that expressed in a PDAC sample having low or control levels of K17. In one embodiment, the increased level of K17 expression that corresponds with a reduced incidence of survival beyond 2 years when compared to a control or standard incidence of survival, is indicated by the detection of K17 expression at a level that is from 11-times greater than the amount of K17 expression detected in a PDAC sample having low or control levels of K17.

In certain embodiments, an increased level of K17 expression that corresponds with a reduced incidence of survival beyond 5 years when compared to a control or standard incidence of survival, is indicated by the detection of K17 expression levels that is from 1-time to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that corresponds with a reduced incidence of survival beyond 5 years when compared to a control or standard incidence of survival, is indicated by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In specific embodiments, the expression an increased level of K17 expression that corresponds with a reduced incidence of survival beyond 5 years when compared to a control or standard incidence of survival, is indicated by the detection of K17 expression levels that is from 5-times to 15-times, 7-times to 14-times, 8-times to 13-times, 9-times to 12-times, 10-times to 12-times or 10-times to 11-times greater than that expressed in a PDAC sample having low or control levels of K17. In one embodiment, the increased level of K17 expression that corresponds with a reduced incidence of survival beyond 5 years when compared to a control or standard incidence of survival, is indicated by the detection of K17 expression at a level that is from 11-times greater than the amount of K17 expression detected in a PDAC sample having low or control levels of K17.

In other embodiments, an increased level of K17 expression is shown by the detection of a 1-fold to 50-fold increase in K17 expression compared to a control or normal level of K17 expression. In other embodiments, an increased level of K17 expression in sample is shown by a 1-fold to 30-fold, 1-fold to 25-fold, 1-fold to 20-fold, 1-fold to 15-fold, 1-fold to 10-fold or 1-fold to 5-fold increase in K17 expression compared to a control or normal level of K17 expression. In yet other embodiments, an increased level of K17 expression in a sample is shown by about a 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold increase in keratin 17 expression over that detected in a control sample. In a specific embodiment, an increased level of K17 expression in a sample is shown when an 11-fold to a 13-fold increase in keratin 17 expression is detected in a PDAC sample when compared to the amount of K17 detected in a control PDAC sample.

In some embodiments of the present disclosure, detection of an increased level of K17 expression in a sample obtained from a subject diagnosed with pancreatic cancer (e.g., PDAC) corresponds to reduction in the likelihood of survival for at least 2 years post diagnosis of about, 50%, 40%, 30%, 20% or 10% when compared to the likelihood of surviving for 2 and/or 5 years post diagnosis exhibited by the average patient diagnosed with pancreatic cancer for which a low or control level of K17 is detected. In other embodiments, detection of an increased level of K17 expression in a sample obtained from a subject diagnosed with pancreatic cancer corresponds to reduction in the likelihood of survival for at least 2 years post diagnosis of from 10% to 50%, 20% to 50%, 30% to 50%, 10% to 20%, 10% to 30%, 10% to 40%, when compared to the likelihood of surviving for 2 and/or 5 years post-diagnosis exhibited by the average patient diagnosed with pancreatic cancer for which a low or control level of K17 is detected. In yet another embodiment, detection of an increased level of K17 expression in a sample obtained from a subject diagnosed with pancreatic cancer reduces the likelihood of survival by at least 30%, when compared to the likelihood of surviving for 2 and/or 5 years post-diagnosis exhibited by the average patient diagnosed with pancreatic cancer for which a low or control level of K17 is detected.

In some embodiments of the present disclosure, detection of an increased level of K17 expression in a sample obtained from a subject diagnosed with pancreatic cancer (e.g., PDAC) corresponds to an increase in hazard of death for the subject. In certain embodiments, the increase in hazard of death associated with detection of an increased level of K17 expression is about 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold or 20-fold when compared to the hazard of death associated patients diagnosed with pancreatic cancer for which a low or control level of K17 is detected. In other embodiments, the increase in hazard of death associated with detection of an increased level of K17 expression is from 1-fold to 5-fold, 1-fold to 4-fold, 1-fold to 3-fold, 1-fold to 2-fold, 2-fold to 5-fold, 2-fold to 4-fold, or 2-fold to 3-fold, when compared to the hazard of death associated patients diagnosed with pancreatic cancer for which a low or control level of K17 is detected. In specific embodiments, the increase in hazard of death associated with detection of an increased level of K17 expression is about 2-fold, when compared to the hazard of death associated patients diagnosed with pancreatic cancer for which a low or control level of K17 is detected.

In some embodiments of the present disclosure, an increased level of K17 expression in a sample identifies the subject as a patient that will not respond positively to surgical resection and/or adjuvant therapy (e.g., treatment with chemotherapy), when compared to a subject exhibiting low or control levels of K17 expression. As such, the present methods can be used to determine whether a subject having pancreatic cancer should be treated by surgical intervention and/or with chemotherapy. In some embodiments, a positive response to chemotherapy is shown by an increase in the likelihood of survival post-treatment for a pancreatic cancer patient, when compared to the average 2 year survival rate for pancreatic cancer patients after undergoing chemotherapy.

The term "chemotherapy" or "adjuvant therapy" as used herein means treatment of a subject diagnosed with cancer (i.e., pancreatic cancer) with a chemical compound, small molecule or antibody that is useful in the treatment of cancer. Chemotherapeutic agents useful in conjunction with the methods described herein include, but are not limited to Folfirinox, cisplatin, carboplatin and/or capecitabine, antimetabolites such as methotrexate and fluoropyrimidine-based pyrimidine antagonist, 5-fluorouracil (5-FU) (Carac® cream, Efudex®, Fluoroplex®, Adrucil®) and S-1; antifolates, including polyglutamatable antifolate compounds; raltitrexed (Tomudex®), GW1843 and pemetrexed (Alimta®) and non-polyglutamatable antifolate compounds; nolatrexed (Thymitaq®), plevitrexed, BGC945; folic acid analogs such as denopterin, methotrexate, pteropterin, trimetrexate; and purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine. In a one embodiment of the current disclosure the chemotherapeutic agent is a nucleoside analog, such as gemcitabine (Gemzar®, Eli Lilly & Co.).

In certain embodiments, a subject diagnosed with pancreatic cancer, for which an increased level of K17 expression in a sample obtained from the subject will not respond positively to chemotherapy. In some embodiments, the pancreatic cancer is PDAC. In other embodiments the subject is diagnosed with pancreatic intraepithelial neoplasia. In certain embodiments, the chemotherapy that a subject for which an increased level of K17 expression is detected, and will not respond to includes treatment with gemcitabine, alone or in combination with, folfirinox, cisplatin, carboplatin and/or capecitabine. In one embodiment, the chemotherapy is gemcitabine.

In certain embodiments, an increased level of K17 expression that indicates that the subject will not respond positively to chemotherapy when compared to a subject exhibiting low or control levels of K17, is indicated by the detection of K17 expression levels that are at least greater than that of a control sample. In one embodiment, an increased level of K17 expression is shown by an increase in the amount of K17 detected in a sample that is at least 1-times, 2-times, 3-times, 4-times, 5-times, 6-times, 7-times, 8-times, 9-times, 10-times, 11-times, 12-times, 13-times, 14-times or 15-times greater than that expressed in a control sample. In certain embodiments, an increased level of K17 expression that indicates that the subject will not respond positively to chemotherapy, is shown by the detection of K17 expression levels that is from 1-time to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that indicates that the subject will not respond positively to chemotherapy is shown by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In specific embodiments, an increased level of K17 expression that indicates that the subject will not respond positively to chemotherapy is shown by the detection of K17 expression levels that is from 5-times to 15-times, 7-times to 14-times, 8-times to 13-times, 9-times to 12-times, 10-times to 12-times or 10-times to 11-times greater than that expressed in a PDAC sample having low or control levels of K17. In one embodiment, the increased level of K17 expression that indicates that the subject will not respond positively to chemotherapy, is indicated by the detection of K17 expression at a level that is from 11-times greater than the amount of K17 expression detected in a PDAC sample having low or control levels of K17.

In other embodiments, a subject having an increased level of K17 expression will not respond positively to surgical resection when compared to a subject exhibiting low or control levels of K17. In such embodiments, the increased amount of K17 expression detected in a PDAC sample that corresponds to the subject from which the sample is obtained not responding positively to surgical resection of the pancreatic cancer is indicated by the detection of K17 expression levels that are at least greater than that of a control sample. In specific embodiments, a positive response to surgical resection is shown by an increase in the likelihood of survival post surgical resection for a patient, when compared to the average 5 year survival rate for pancreatic cancer patients post surgical resection.

In one embodiment, an increased level of K17 expression is shown by an increase in the amount of K17 detected in a sample that is at least 1-times, 2-times, 3-times, 4-times, 5-times, 6-times, 7-times, 8-times, 9-times, 10-times, 11-times, 12-times, 13-times, 14-times or 15-times greater than that expressed in a control sample. In other embodiments, an increased level of K17 expression that indicates that the subject will not respond positively to surgical resection of the pancreatic tumor, is shown by the detection of K17 expression levels that is from 1-time to 50-times, 1-time to 40-times, 1-time to 30-times, 1-time to 20-times, 1-time to 15-times, 1-time to 10-times or 1-time to 5-times greater than that expressed in a PDAC sample having low or control levels of K17. In other embodiments, an increased level of K17 expression that indicates that the subject will not respond positively to surgical resection of the pancreatic tumor, is shown by the detection of K17 expression levels that is from 2-times to 20-times, 3-times to 20-times, 4-times to 20-times, 5-times to 20-times, 6-times to 20-times, 7-times to 20-times, 8-times to 20-times, 9-times to 20-times, 10-times to 20-times or 10-times to 15-times greater than that expressed in a PDAC sample having low or control levels of K17. In specific embodiments, an increased level of K17 expression that indicates that the subject will not respond positively to surgical resection of the pancreatic tumor, is shown by the detection of K17 expression levels that is from 5-times to 15-times, 7-times to 14-times, 8-times to 13-times, 9-times to 12-times, 10-times to 12-times or 10-times to 11-times greater than that expressed in a PDAC sample having low or control levels of K17. In one embodiment, the increased level of K17 expression that indicates that the subject will not respond positively to surgical resection of the pancreatic tumor, is indicated by the detection of K17 expression at a level that is from 11-times greater than the amount of K17 expression detected in a PDAC sample having low or control levels of K17.

In some embodiments, the increase in K17 expression detected in a sample that corresponds to subject's inability to respond positively to chemotherapy and/or surgical resection is about 1-fold to 20-fold, 5-fold to 20-fold, 5-fold to 15-fold, 10-fold to 20-fold or 10-fold to 15-fold over that detected in a control sample. In other embodiments, the increase in K17 expression detected in a sample that corresponds to subject's inability to respond positively to chemotherapy and/or surgical resection is about a 11-fold to about a 13-fold increase in keratin 17 expression compared to the amount of K17 detected in a control sample.

Taken together, the current disclosure provides methods for determining the likelihood of survival of a subject that has been diagnosed with pancreatic cancer or PDAC by detecting the level of K17 expression in a sample; and determining whether the level of K17 is increased in the sample, when compared to other control pancreatic cancer samples that exhibit low or normal levels of K17 or in the test sample. Whereby detection of an increased level of K17 expression in a pancreatic cancer sample identifies a subject as having the greatest risk for pancreatic cancer mortality, not responding positively to surgical resection and/or chemotherapeutic treatment.

EXAMPLES

The following examples further illustrate the disclosure, but should not be construed to limit the scope of the disclosure in any way.

Example 1. Materials and Methods

Patient Tissue Sampling.

The present disclosure analyzed a patient population including 268 subjects diagnosed with PDAC. A total of 117 formalin-fixed paraffin-embedded surgical tissue blocks from PDAC cases were retrospectively (2008-2012) selected from the archival collections of Stony Brook University and UMass Memorial Medical Center. The criteria for selection were (i) diagnosis of primary PDAC (ii) >18 years at time of diagnosis (iii) and negative resection margins. Patients with a diagnosis of cancer that were primary at other anatomic sites were excluded. PDACs were classified by tumor stage according to the original surgical pathology report. The histologic grade was re-assessed in all cases by a single pathologist. Survival and adjuvant therapy data was obtained from UMass Memorial Cancer Registry and Stony Brook Medicine Cancer Registry. All protocols were approved by the IRBs of both institutions.

K17 mRNA expression levels were analyzed using The Cancer Genome Atlas (TCGA) Pancreatic Adenocarcinoma database. Biankin A V, et al. *Nature*. 2012; 491 pp. 399-405. Out of the 186 pancreatic cancer samples for which RNA Sequencing data (RNASeq V2 RSEM) was available, only 151 PDAC cases had both sequence data and survival information. All clinical information was based on the original pathologist report. In addition, mutation data from whole exome sequence was obtained for 91 cases with 78 having survival information.

K17 Protein Analysis.

To identify and quantify K17 protein expression, immunohistochemistry was performed by an indirect immunoperoxidase method to identify the presence of K17 protein. Briefly, after incubation at 60° C., PDAC samples were sliced, deparaffinized in xylene, and rehydrated in alcohols. Antigen retrieval was performed in citrate buffer at 120° C. for 10 minutes in a decloaking chamber. Endogenous peroxidase was blocked by 3% hydrogen peroxide and sections were incubated overnight at 4° C. with: Mouse monoclonal-[E3] anti-human K17 antibody (Abcam, Cambridge, Mass.). After primary antibody, biotinylated-horse secondary antibodies (R.T.U. Vectastain ABC kit; Vector Laboratories, Burlingame, Calif.) were added for detection of binding between the primary, Mouse monoclonal-[E3] anti-human K17 antibody and K17 protein in the sample. Development was carried out with 3, 3' diaminobenzidine (DAB) (Dako, Carpinteria, Calif.), and counter-stain was done with hematoxylin. Negative controls were performed on all runs using an equivalent concentration of a subclass-matched immunoglobulin.

Immunohistochemical stains for K17 in PDACs were scored by PathSQ, a manual semi-quantitative scoring system, which quantifies the percentage of strongly stained tumor cells, blinded to corresponding clinical data. In certain cases, slides were scored by the National Institutes of Health ImageJ 1.46, Java-based image processor software using the DAB-Hematoxylin (DAB-H) color deconvolution plugin. See Schneider C A, et al., *Nat methods*. (2012) 9:671-5 and/or by a manual semi-quantitative scoring system, which quantifies the percentage of strong-positively stained cells blinded to corresponding clinical data (PathSQ).

Statistical Analysis.

Continuous data are described using means±standard deviation. Statistical significance between the means of two groups was determined using Student's T-test or Mann-Whitney U tests. Statistical comparisons of the means of multiple groups were determined using one-way ANOVA or Kruskal-Wallis ANOVA by ranks. Patient samples were grouped into meaningful categories based on their clinical characteristics. Tumor stages were grouped according to localized disease (IA/IB/IIA) and metastatic disease (IIB/III/IV), histological grades were grouped as low grade (well differentiated-G1) and high grade (moderately/poorly differentiated-G2 and G3, respectively), primary tumor was grouped as low (T1 & T2) and high (T3 & T4), and node status as positive (N1) and negative (N0).

In the protein data set, the K17 score cutoff point for increased (high) K17 expression level or control (low) K17 expression levels detected in a sample was 25 (i.e., 25% PathSQ score, or for mRNA a 75% percentile of K17 samples) based on the minimum Akaike's Information Criterion (AIC) level for all possible K17 high/low cutoff points. In the TCGA data, the K17 mRNA amount ranged from 2.41 to 170,437.66, a range of 5 orders of magnitude. No clinically intuitive data transformation of K17 mRNA amount yielded a normally distributed variable. Therefore, the K17 mRNA amount for each patient was transformed into its percentile rank for these analyses. Based on the minimum AIC, patients with K17 mRNA percentiles less than 49 (raw value=6372.1) were classified with control (low) K17 expression and all samples for which K17 mRNA expression was in the $49^{th}$ percentile or greater were classified exhibiting increased (high)-K17 expression.

Overall patient survival was calculated from the date of surgery to the date of death from pancreatic cancer and was estimated using the Kaplan-Meier method, using median or rate at specific time points with 95% confidence interval. Alive patients were censored at the last follow-up; patients that died from another cause were also censored. Univariate analyses compared survival for keratin 17 expression level (low vs. high), tumor stage, histological grade, primary tumor, and node status. To examine overall survival rates while adjusting for potential confounders, multivariate analyses were performed by Cox proportional hazards regression. Four bivariate analyses (without an interaction term) compared survival for keratin 17 expression levels and one of the clinical characteristics and eight stratified analyses compared survival for keratin 17 expression levels within each individual group. Internal validity of the model was assessed by a bootstrap sample procedure and jackknife analyses. The relative and attributable risk of high keratin 17 expression levels was assessed.

For the mRNA data set, additional stratified analyses compared survival for keratin 17 levels within these groups: resection type, treatments (yes or no)—chemotherapy and radiation therapy, and mutation status (yes or no) for KRAS, $p16^{INK4a}$, TP53, and SMAD4. Univariate analyses were also run for each mutation status. Mutated KRAS status included missense mutations at codons G12V/D/R. All genetic alterations, including point mutations, frame shifts and deletions, were grouped and classified as "altered" for $p16^{INK4a}$, TP53, and SMAD4 genes. REMARK recommendations for tumor marker prognostic studies were followed according to known protocol, as described in Ballehaninna U K, et al., *J Gastrointest Oncol*. 2012; 3 pp. 105-19. All sample analyses were performed using SAS 9.3 (SAS Institute, Inc., Cary, N.C.) and SigmaPlot 11 (Systat Software, San Jose, Calif.). Statistical significance was set at $p<0.05$ (a).

K17 protein (n=117) and mRNA (n=151) levels were studied in pancreatic cancer samples and were compared to clinicopathologic features, including survival, by retrospective analyses. Furthermore, stratified analyses of KRAS, TP53, $p16^{INK4a}$ and SMAD4 driver mutations and K17 status were evaluated in the context of patient outcome (n=78).

Example 2. Patient Characteristics and K17 Status

Clinical Characteristics.

Pancreatic cancer patients that were evaluated for K17 protein expression levels were similar to those evaluated for K17 mRNA expression levels, except that patients evaluated by immunohistochemistry (i.e., protein detection) had longer mean follow-up time. No significant differences in K17 expression levels were found across different tumor stages, tumor grades, primary-tumor size and lymph node status. PDACs were classified as having control (low) K17 expression levels or increased (high) K17 expression levels based on K17 protein or mRNA levels (FIGS. 1A-D and 2A-D). More than half of the pancreatic cancer samples analyzed were determined to have increased K17 expression levels that were, on average 11-times higher compared to corresponding control (low) K17 counterparts (FIGS. 1A-C).

Mutational analysis of the K17 transcripts detected was conducted. mRNA expression and mutation analysis data showed that K17 in PDAC samples analyzed was wild-type, as no mutations were found in K17 mRNA.

Additionally pancreatic tissue that included pancreatic cancer precursor lesions, such as pancreatic ductal intraepithelial neoplasias (PanINs), intraductal papillary mucinous neoplasm (IPMN), and acinar-to-ductal metaplastic ducts were analyzed for K17 expression. Analysis of PanINs obtained from patients diagnosed with PDAC that exhibit increased K17 expression also exhibited increased K17 protein expression (FIG. 2A, right), while PanINs of low-K17 PDACs expressed low to no K17 (FIG. 4A, left). In addition, intraductal papillary mucinous neoplasm (IPMN) had minimal expression of K17 (FIG. 4B), but, K17 was expressed in acinar-to-ductal metaplastic ducts (FIG. 4C). Furthermore, there was minimal to no expression of K17 in mature acinar cells and islet cells (FIG. 4C-4D).

Example 3. Univariate and Multivariate Analyses for Overall Patient Survival

The association between a subject's clinical characteristics and K17 expression level with risk of death was assessed by univariate and multivariate Cox regression analyses, the results of which are in Table 1. Univariate and multivariate analyses identified K17 expression level, tumor stage and tumor grade as three independent significant prognostic factors (Table 1), but only K17 expression level was significant in both data sets. Neither primary tumor size, nor lymph node status were associated with a statistically significant increase or decrease overall survival patient survival (Table 1, FIG. 3A-C).

In contrast, the univariate analysis shown in Table 1 and FIG. 3A-C shows that increased (high) K17 expression coincides with a statistically significant decrease in overall survival patient survival, as evidenced by the approximate two-fold increase in hazard of death after diagnosis. In all multivariate models, combining K17 expression and clinical-pathology characteristics, K17 expression levels added significant survival information to the risk of death assessment after diagnosis (Table 1). Taken together, these data show that K17 expression provides additional survival information to the current model of prognosis assessment for PDACs.

Example 4. Stratified Analyses for Overall Survival

Next, synergistic effects of K17 expression and patient clinical characteristics was examined for a potential effect on patient outcome. Stratified analyses determined that increased K17 expression in a PDAC tumor sample increased hazard of death by 50% after diagnosis of a patient with metastatic and poorly differentiated tumors. See FIG. 6A-D. As shown in FIG. 6A-D, there was a significant correlation between K17 expression levels detected in a PDAC sample and tumor stage, histological grade and node status. In both the protein (FIGS. 6A & C) and mRNA dataset (FIGS. 6B & D), K17 expression was a significant prognostic indicator of patient survival for moderately/poorly differentiated tumors (FIGS. 6C & D), and high stage (FIGS. 6A & C) but not for low stage tumors. As such, these data indicate that increased K17 expression was a significant predictor of survival for pancreatic cancer patients diagnosed with all grades and stages of tumor.

Further, FIG. 6A-D shows K17 expression-based survival probabilities of pancreatic cancer patients using protein or mRNA expression with Kaplan-Meier curves for stratified analyses for metastatic disease and poorly differentiated tumors. Overall, increased (high) K17 expression was found to correlate with lower survival probabilities (FIG. 2A-D). Specifically, when K17 protein expression levels in a sample were analyzed it was determined that, among patients with metastatic pancreatic cancer (stage IIB, III and IV), subjects having PDAC with control (low) levels of K17 expression had a two-year survival probability of 50%, which is comparable to other studies of patients with localized disease Bilimoria K Y, et al. *Cancer.* 2007; 110 pp. 738-44.

In contrast, increased K17 expression in a PDAC sample resulted in a two-year survival probability of <20%. Similar differences in survival probabilities were also found using K17 expression detection based on K17 mRNA expression levels (FIGS. 6B & D). Furthermore, based on risk of death calculations it was determined that the relative risk of death for patients exhibiting increased K17 expression (protein and/or mRNA levels), was between 144.6-161.0%, suggesting that for every 100 deaths for patients having control levels of K17 expression between 144 to 161 deaths occur in pancreatic cancer patients expressing increased levels of K17. Stated another way, the attributable risk of death to increased K17 expression in a PDAC sample was between 26.6% and 27.2%, suggesting that for every 100 deaths in the patients expressing increased levels of K17, 26 to 27 deaths would not have occurred if such patients expressed control levels of K17.

Overall, these data show that K17 expression alone is a biological marker that stratifies survival probabilities within pancreatic cancer patients at advanced-stages or with poorly-differentiated tumors, narrowing the confidence intervals in survival predictions across PDAC patients with similar characteristics.

The prognostic value of increased K17 expression was further validated by assessing PDAC clinical outcome in three ways. First, the improvement in the Akaike information criterion (AIC) in the models with and without K17 status was assessed. In each case, the AIC improvement was statistically significant with p-values comparable to those for the analogous K17 hazard-ratio values from the multivariate analyses. See Table 1. Second, as shown in Table 3, bootstrap analyses was performed with 1,000 repetitions for each model and found that all K17 hazard ratios were above 1.00 indicating a statistically significant relationship between increased K17 expression and patient outcome. Third, jackknife analysis was performed, which identified that all K17 hazard ratios fell within the low and high jackknife hazard ratios estimates (Table 3), and all of ratios were above 1.00, showing that reliance on K17 expression was not overly influenced by a single case.

Example 5. Increased K17 Expression was Detected in Greater than 70% of PDAC Cases Analyzed, but not Associated with K17 Gene-Copy Number In order to determine whether K17 expression alone was indicative of patient prognosis, patient survival and clinical outcome, PDAC samples were analyzed to determine if alterations in well known genetic mutations that are associated with pancreatic cancer development and progression play a role in patient prognosis, patient survival and clinical outcome. FIG. 7A-H shows that increased (high) K17 expression alone, not genetic mutations, correlated with patient outcome.

Specifically, as shown in FIG. 7A-H well known mutations in the oncogene KRAS and tumor suppressor genes, TP53, p16$^{INK4a}$ (CDKN2A) KMT2C, TGFBR2, ATM, ARID1A and SMAD4 were analyzed in PDAC patient samples to determine if alterations in these genes predicted patient outcome. In no case there was a significant association with overall survival. Here, patients with wild-type KRAS, p16$^{INK4a}$, SMAD4 or altered TP53 and high-K17 status had decreased survival probabilities and hazard ratios >2. Surprisingly, the hazard ratio for patients with wild-type KRAS and increased K17 expression was greater than 11. Taken together, these results teach that somatic mutation profiles in PDAC patients are not the primary determinant of long-term survival and clinical outcome.

Example 6. K17 Expression in a PDAC Patient Sample is a Prognostic Indicator for a Subject's Response to Surgical Resection and Adjuvant Chemotherapy PDAC patients who undergo resection are commonly treated with adjuvant therapy, such as with chemotherapeutic agents (e.g., gemcitabine). These, pancreatic cancer patients have, on average, improved survival times post surgical intervention, yet there is a wide range of treatment responses and outcomes, as up to 20% of all resected patients survive 5 years after resection. See Sinn M, et al. *J Surg Oncol.* 2013; 108 pp. 398-402. Since, in the present disclosure, increased K17 expression in a sample obtained from PDAC patients shows prognostic value, K17's use in determining a subject's response to treatment was also studied.

As shown in Table 3, resected tumors by pancreatoduodenectomy or "Whipple" for which an increased level of K17 expression was detected status were significantly associated with poorer patient outcome than those for which a control (low) level of K17 expression was detected.

Furthermore, FIGS. 4A-D and 5A-D, clearly show that increased expression of K17 in a patient tumor sample was associated with a poor response to chemotherapy (Gemcitabine), and patient survival probability decreased by 50% when compared to pancreatic cancer patients that exhibit low-K17 expression. See, also Table 3. Specifically, as shown in FIGS. 4A-D and 5A-D, patients for which control levels of K17 expression was detected were significantly more responsive to treatment with chemotherapy (Gemcitabine) as evidenced by the significant increase in overall survival of patients exhibiting control (low) levels of K17 when compared to subjects treated with gemcitabine that exhibit increased K17 expression.

Unexpectedly, no correlation between K17 expression and a response to radiotherapy was detected, as results for K17 protein and mRNA levels were inconsistent. Finally, as shown in Table 3, it was determined that PDAC patients who did not receive targeted therapy and have increased K17 expression levels had decreased survival probabilities. Hence, increased K17 expression in a PDAC sample is a clear indicator of a poorer response to surgical resection.

Example 7. Clinical Relevance and Patient Outcome

Previous literature has reported that approximately 20% of all PDACs are defined as "very-long term survivors" (VLTS). See e.g., Dal Molin M, et al. *Clin Cancer Res.* 2015; 21 pp. 1944-50. However, clinical outcome and pancreatic cancer patient survival is highly unpredictable and not well understood. For example, the current understanding of the biological factors that contribute to this extended survival is limited, as clinicopathologic features and/or genetic landscape differences do not explain such differences. Id. Although only the 10$^{th}$ most commonly diagnosed cancer, PDAC is the fourth most common cause of cancer death in the U.S (see, Siegel R L, et al. *CA Cancer J Clin.* 2015; 65 pp.-29), suggesting that its treatment response is far more unpredictable than other more common cancers. Further to the unpredictable nature of PDAC treatment, a critical challenge in metastatic pancreatic cancer is to predict response to surgical resection and chemotherapy as only 35% cases respond to adjuvant therapy and 80% of cases die within the first two years. Sinn M, et al. *J Surg Oncol.* 2013; 108 pp. 398-402. These differences in patient outcome are attributable in part to the differences underlying in tumor biology. Ryan D P, et al. *N Engl J Med.* 2014; 371 pp. 2140-1.

Here, the inventors have determined that about 40% of PDAC subjects for which a low or control level K17 expression was detected had twice the median survival probabilities when compared to those for which a increased level of K17 expression was detected. See FIG. 3. This shows, among other things, that K17 expression is a determinant marker of pancreatic cancer patient prognosis and clinical outcome. Additionally, the present disclosure shows that increased K17 expression in pancreatic cancer samples is associated with poorer overall survival of the patient and a poor response to surgical resection and adjuvant therapy with Gemcitabine, when compared to pancreatic cancer patients exhibiting a control level of K17 expression.

Further, using tissue biorepositories and RNA sequencing data from PDACs, where clinical and survival information were available it was shown that both protein and mRNA expression levels of K17 can be used as prognostic markers in patients with metastatic pancreatic cancer and/or poorly differentiated pancreatic tumors. This study, which includes an analysis of approximately 300 pancreatic cancer patient samples, determined the K17 threshold based on the cut-off value of increased and control K17 expression values that predicted the strongest survival model, showing that both K17 protein and mRNA expression levels could be used as prognostic markers in pancreatic cancer.

Taken together, the present disclosure provides the first recognition of the prognostic and predictive value of K17 expression in PDACs. The specific examples to follow demonstrate that K17 is differentially expressed across PDACs and provides prognostic and predictive information at baseline, providing additional survival and a priori treatment response prediction. Consequently, K17 represents a novel biomarker that allows stratification of prognostic groups at the time of surgical resection, highlighting PDAC cases with more aggressive tumors at lower survival probabilities under common treatment.

TABLE 1

Univariate and Multivariate analyses of overall patient survival for each cohort analyzed using a Cox proportional hazards model.

| | Univariate Analysis | | Multivariate Analysis | |
| --- | --- | --- | --- | --- |
| | Hazard ratio (95% CI) | p-value | Hazard ratio (95% CI) | p-value |
| PDAC Cohort A (mRNA; n = 94) | | | | |
| High K17 | 1.83 (1.04-3.25) | 0.036 | 1.01 (0.55-2.2) | 0.775 |
| Tumor stage, per increase | 1.38 (0.93-2.05) | 0.927 | 1.47 (0.95-2.28) | 0.090 |
| Tumor grade, per increase | 1.64 (1.07-2.50) | 0.021 | 1.93 (1.14-3.27) | 0.010 |

TABLE 1-continued

Univariate and Multivariate analyses of overall patient survival for each cohort analyzed using a Cox proportional hazards model.

|  | Univariate Analysis | | Multivariate Analysis | |
|---|---|---|---|---|
|  | Hazard ratio (95% CI) | p-value | Hazard ratio (95% CI) | p-value |
| Age, 10 year increment | 1.02 (0.94-1.63) | 0.120 | 1.03 (0.97-1.8) | 0.070 |
| Gender, Male to female | 0.93 (0.55-1.54) | 0.770 | 0.85 (0.50-1.48) | 0.561 |
| PDAC Cohort B (mRNA; n = 177)) | | | | |
| High K17 | 1.56 (1.01-2.41) | 0.044 | | |
| Tumor stage, per increase | | | | |
| Tumor grade, per increase | | | | |
| Age, 10 year increment | | | | |
| Gender, Male to female | | | | |
| PDAC Cohort C (mRNA; n = 170) | | | | |
| High K17 | 2.20 (1.26-3.85) | 0.005 | 2.33 (1.31-4.14) | 0.004 |
| Tumor stage, per increase | 1.81 (0.88-3.71) | 0.102 | 1.81 (0.86-3.79) | 0.114 |
| Tumor grade, per increase | 1.65 (1.15-2.4) | 0.068 | 1.44 (0.98-2.12) | 0.062 |
| Age, 10 year increment | 1.02 (0.98-1.64) | 0.060 | 1.02 (0.97-1.64) | 0.081 |
| Gender, Male to female | 0.76 (0.45-1.30) | 0.320 | 0.87 (0.51-1.50) | 0.616 |
| SBU PDAC Cohort D (Protein; n = 117) | | | | |
| High K17 | 2.18 (1.30-3.65) | 0.003 | 2.51 (1.46-4.34) | 0.001 |
| Tumor stage, per increase | 4.29 (1.18-15.56) | 0.026 | 3.95 (1.11-13.98) | 0.033 |
| Tumor grade, per increase | 1.57 (1.16-2.42) | 0.006 | 1.46 (0.99-2.15) | 0.051 |
| Age, 10 year increment | 0.99 (0.77-1.24) | 0.843 | 0.99 (0.76-1.26) | 0.852 |
| Gender, female to male | 1.08 (0.68-1.73) | 0.735 | 1.24 (0.49-1.33) | 0.404 |

TABLE 2

Prognostic value of gene mutations (univariate) and interaction with K17 mRNA expression level status in overall patient survival.

|  | Effect of changing Keeping constant | N | Wald Chi-Square | Hazard Ratio (HR) | 95% CI for HR | p-value |
|---|---|---|---|---|---|---|
| Univariate analysis KRAS status | | | | | | |
| Wild-type vs mutant p16$^{INK4a}$ status | | 78 | 0.73 | 1.33 | 0.4-1.44 | 0.3927 |
| Wild-type vs mutant TP53 status | | 78 | 1.05 | 1.44 | 0.35-1.39 | 0.3059 |
| Wild-type vs mutant SMAD4 status | | 78 | 0.04 | 0.94 | 0.57-1.96 | 0.8513 |
| Wild-type vs mutant Stratified analysis | | 78 | 0.93 | 1.41 | 0.36-1.42 | 0.3341 |
| Low vs High K17 | Wild-type KRAS | 25 | 8.96 | 11.91 | 2.35-60.25 | 0.0028 |
| Low vs High K17 | Mutated KRAS | 53 | 1.10 | 1.46 | 0.72-2.94 | 0.2950 |
| Low vs High K17 | Wild-type p16$^{INK4a}$ | 60 | 8.07 | 2.78 | 1.37-5.62 | 0.0045 |
| Low vs High K17 | Altered p16$^{INK4a}$ | 18 | 0.02 | 1.08 | 0.33-3.56 | 0.9008 |
| Low vs High K17 | Wild-type TP53 | 28 | 2.23 | 2.15 | 0.79-5.90 | 0.1356 |
| Low vs High K17 | Altered TP53 | 50 | 5.23 | 2.45 | 1.14-5.28 | 0.0222 |
| Low vs High K17 | Wild-type SMAD4 | 64 | 7.29 | 2.74 | 1.32-5.70 | 0.0069 |
| Low vs High K17 | Altered SMAD4 | 14 | 1.78 | 2.48 | 0.65-9.40 | 0.1820 |

TABLE 3

Bootstrap and jackknife statistical validation of results obtained based on control (low) levels of K17 expression and increased (high) levels of K17 expression.

| All Survival Data | K17 Protein Expression (N = 117) | | | K17 mRNA Expression (N = 151) | | |
|---|---|---|---|---|---|---|
| Bootstrap Analyses (n = 1000) in the stratified model that included: | K17 HR | Low BS 95% CI | High BS 95% CI | K17 HR* | Low BS 95% CI | High BS 95% CI |
| Clinical Stage IA/IB/IIA | 1.36 | 0.53 | 5.01 | 3.08 | 0.88 | 15.93 |
| Clinical Stage IIB/III/IV | 2.59 | 1.47 | 4.70 | 1.69 | 1.05 | 2.95 |
| Histologic Grade G1 | 1.50 | 0.19 | ∞ | 17.33 | 3.85 | ∞ |
| Histologic Grade G2 + G3 | 2.07 | 1.18 | 3.53 | 1.67 | 1.05 | 2.74 |
| Primary Tumor T1 + T2 | 3.13 | 1.20 | 12.86 | 1.92 | 0.51 | 12.22 |
| Primary Tumor T3 + T4 | 1.76 | 1.03 | 3.26 | 2.06 | 1.27 | 3.62 |
| Lymph node status N0 | 1.20 | 0.49 | 3.31 | 3.08 | 0.88 | 15.93 |
| Lymph node status N1 | 2.72 | 1.55 | 5.26 | 1.75 | 1.03 | 3.13 |
| Jackknife Analyses in the stratified model that included: | K17 HR* | Low JK CI | High JK CI | K17 HR* | Low JK CI | High JK CI |
| Clinical Stage IA/IB/IIA | 1.36 | 1.12 | 1.67 | 3.08 | 2.71 | 4.30 |
| Clinical Stage IIB/III/IV | 2.59 | 1.47 | 4.70 | 1.69 | 1.59 | 1.87 |
| Histologic Grade G1 | 1.50 | 1.06 | 2.25 | 17.33 | 15.19 | ∞ |
| Histologic Grade G2 + G3 | 2.07 | 1.90 | 2.19 | 1.67 | 1.59 | 1.80 |
| Primary Tumor T1 + T2 | 3.13 | 2.57 | 4.19 | 1.92 | 1.58 | 2.65 |
| Primary Tumor T3 + T4 | 1.76 | 1.67 | 1.86 | 2.06 | 1.95 | 2.29 |
| Lymph node status N0 | 1.20 | 1.03 | 1.38 | 3.08 | 2.71 | 4.30 |
| Lymph node status N1 | 2.72 | 2.48 | 2.95 | 1.75 | 1.62 | 1.94 |

What is claimed is:

1. A method for identifying a subject with pancreatic cancer comprising:
   (a) detecting the amount of Keratin 17 (K17) mRNA expression in a sample obtained from said subject;
   (b) detecting the amount of K17 mRNA expression in a control sample; and
   (c) calculating a percentile rank of the detected amount of K17 mRNA expression in said sample, as compared to a set of sample expression levels of K17 mRNA, wherein when the percentile rank in said sample is less than the $49^{th}$ percentile, the subject is identified as having a pancreatic cancer that will respond positively to treatment with chemotherapy; and
   (d) treating said subject with pancreatic cancer by administering a chemotherapeutic agent to the subject.

2. The method of claim 1, wherein said pancreatic cancer is pancreatic ductal carcinoma (PDAC).

3. The method of claim 1, wherein the detected amount of K17 mRNA in said sample is at least 11-times greater than that detected in said control sample.

4. The method of claim 1, wherein the chemotherapeutic agent is selected from the group consisting of gemcitabine, folfirinox, cisplatin, carboplatin and capecitabine.

5. The method of claim 4, wherein the chemotherapeutic agent is gemcitabine.

6. The method of claim 1, wherein the sample is a pancreatic tissue sample obtained from the subject.

7. The method of claim 6, wherein the pancreatic tissue sample is obtained by tissue biopsy.

8. The method of claim 1, wherein the sample is a blood sample obtained from the subject.

9. The method of claim 6, wherein the control sample is a tissue sample obtained from a healthy subject.

10. The method of claim 6, wherein the control sample is a blood sample obtained from a healthy subject.

11. The method of claim 1, wherein the pancreatic cancer is pancreatic ductal intraepithelial neoplasias (PanINs) or intraductal papillary mucinous neoplasm (IPMN).

12. The method of claim 1, wherein the amount of K17 mRNA expression in said sample and said control sample is detected by quantitative-Reverse Transcriptase (RT)-PCR, microarray analysis, or RT-PCR.

13. A method for identifying a subject with pancreatic cancer comprising:
   (a) detecting the amount of K17 protein expression in a tissue sample obtained from said subject using a PathSQ scoring system, wherein the subject is identified as having pancreatic cancer that will respond positively to treatment with chemotherapy when a PathSQ of less than 25%, wherein the PathSQ scoring system comprises a manual semi-quantitative scoring system, which quantities the percentage of strong-positively stained cells blinded to a corresponding clinical data; and
   (b) administering a chemotherapeutic agent to the subject.

14. The method of claim 13, wherein said detecting the amount of K17 protein expression comprises contacting each of said sample and said control sample with a mouse monoclonal antibody or a rabbit monoclonal [EP1623] anti-human K17 antibody that binds K17 protein and determining the amount of K17 protein bound to said antibody.

15. The method of claim 13, wherein said pancreatic cancer is pancreatic ductal carcinoma (PDAC).

16. The method of claim 13, wherein the pancreatic cancer is pancreatic ductal intraepithelial neoplasias (PanINs) or intraductal papillary mucinous neoplasm (IPMN).

17. The method of claim 13, wherein the chemotherapeutic agent is selected from the group consisting of gemcitabine, folfirinox, cisplatin, carboplatin and capecitabine.

18. The method of claim 17, wherein the chemotherapeutic agent is gemcitabine.

19. The method of claim 13, wherein the sample is a pancreatic tissue sample obtained from the subject.

20. The method of claim 19, wherein the pancreatic tissue sample is obtained by tissue biopsy.

21. The method of claim 19, wherein the pancreatic tissue sample is a formalin-fixed, paraffin-embedded sample.

* * * * *